US008834883B2

(12) United States Patent
Croy et al.

(10) Patent No.: US 8,834,883 B2
(45) Date of Patent: Sep. 16, 2014

(54) ANTI-VEGF ANTIBODIES AND USES THEREOF

(75) Inventors: Leslie A. Croy, Lakeville, NY (US); Mark J. Paris, Mendon, NY (US); Ernest S. Smith, Ontario, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 13/703,947

(22) PCT Filed: Jun. 14, 2011

(86) PCT No.: PCT/US2011/040361
§ 371 (c)(1),
(2), (4) Date: Feb. 28, 2013

(87) PCT Pub. No.: WO2011/159704
PCT Pub. Date: Dec. 22, 2011

(65) Prior Publication Data
US 2013/0202615 A1    Aug. 8, 2013

Related U.S. Application Data

(60) Provisional application No. 61/354,590, filed on Jun. 14, 2010.

(51) Int. Cl.
| | | |
|---|---|---|
| C07K 16/22 | (2006.01) | |
| C07K 14/475 | (2006.01) | |
| G01N 33/53 | (2006.01) | |
| A61K 51/10 | (2006.01) | |
| A61K 47/48 | (2006.01) | |
| A61K 39/395 | (2006.01) | |

(52) U.S. Cl.
USPC ............. 424/158.1; 424/145.1; 424/130.1; 424/178.1; 424/179.1; 424/181.1; 424/183.1; 530/387.3; 530/388.15; 530/388.24; 530/391.3; 530/391.7

(58) Field of Classification Search
None
See application file for complete search history.

(56) References Cited

U.S. PATENT DOCUMENTS

| | | |
|---|---|---|
| 6,884,879 B1 | 4/2005 | Baca et al. |
| 2002/0032315 A1 | 3/2002 | Baca et al. |
| 2005/0118643 A1 | 6/2005 | Burgess et al. |
| 2006/0165681 A1 | 7/2006 | Ellis et al. |
| 2006/0280747 A1 | 12/2006 | Fuh et al. |
| 2009/0060924 A1 | 3/2009 | Korytko et al. |
| 2009/0142343 A1 | 6/2009 | Fuh et al. |
| 2009/0297449 A1 | 12/2009 | Devy |
| 2010/0004431 A1 | 1/2010 | Bernett et al. |

FOREIGN PATENT DOCUMENTS

| | | |
|---|---|---|
| WO | WO 2010/032061 A1 | 3/2010 |
| WO | WO 2010/061991 A1 | 6/2010 |

OTHER PUBLICATIONS

Paul, et al.. ed., Fundamental immunology, 3rd ed., p. 242, 292-295, 1993.*
Rudikoff et al., Proc. Natl. Acad. Sci. USA, 79(6):1979-1983, Mar. 1982.*
Colman et al., Research in Immunology, 145:33-36, 1994.*
MacCallum et al. J. Mol. Biol., 262, 732-745, 1996.*
Wu et al., J. Mol. Biol. 294: 151-162, 1999.*
Yu et al., Investigative Ophthalmology & Visual Science 49(2): 522-527, Feb. 2008.*
Bendig et al., Methods: A Companion to Methods in Enzymology, 8:83-93, 1995.*
Dougher, M. and Terman, B.I., "Autophosphorylation of KDR in the kinase domain is required for maximal VEGF-stimulated kinase activity and receptor internalization," Oncogene, 1999, vol. 18, pp. 1619-1627.
Ferrara, N., "VEGF and the quest for tumour angiogenesis factors," Nature Reviews, 2002, vol. 2, pp. 795-803.
Ferrara, N., et al., "The biology of VEGF and its receptors," Nature Med., 2003, vol. 9, No. 6, pp. 669-676.
Gerber, H-P. and Ferrara, N., "Pharmacology and Pharmacodynamics of Bevacizumab as Monotherapy or in Combination with Cytotoxic Therapy in Preclinical Studies," Cancer Res., 2005, vol. 65, No. 3, pp. 671-680.
Hicklin, D.J. and Ellis, L.M., "Role of the Vascular Endothelial Growth Factor Pathway in Tumor Growth and Angiogenesis," J. Clin. Oncol., 2005, vol. 23, No. 5, pp. 1011-1027.
Ho, Q.T. and Kuo, C.J., "Vascular endothelial growth factor: Biology and therapeutic applications," Intl J. Biochem. Cell Biol., 2007, vol. 39, pp. 1349-1357.
Kim, K.J., et al., "Inhibition of vascular endothelial growth factor-induced angiogenesis suppresses tumour growth in vivo," Nature, 1993, vol. 362, pp. 841-844.
Pander, J., et al., "Pharmacogenetics of EGFR and VEGF inhibition," Drug Discovery Today, 2007, vol. 12, Nos. 23/24, pp. 1054-1060.
Presta, L.G., et al., "Humanization of an Anti-Vascular Endothelial Growth Factor Monoclonal Antibody for the Therapy of Solid Tumors and Other Disorders," Cancer Res., 1997, vol. 57, pp. 4593-4599.
Yu, Y., et al., "A Humanized Anti-VEGF Rabbit Monoclonal Antibody Inhibits Angiogenesis and Blocks Tumor Growth in Xenograft Models," PLoS One, 2010, vol. 5, Issue 2, pp. 1-12.

* cited by examiner

Primary Examiner — Phuong Huynh
(74) Attorney, Agent, or Firm — Alston & Bird LLP

(57) ABSTRACT

Provided are monoclonal antibodies and antigen binding fragments thereof that specifically bind vascular endothelial growth factor (VEGF). The anti-VEGF monoclonal antibodies block VEGF binding to its receptors (e.g., VEGFR1 and/or VEGFR2) and prevent phosphorylation of VEGFR2 by VEGF. Also provided are methods of using the monoclonal anti-VEGF antibodies for treatment of disease, including cancer.

34 Claims, 6 Drawing Sheets

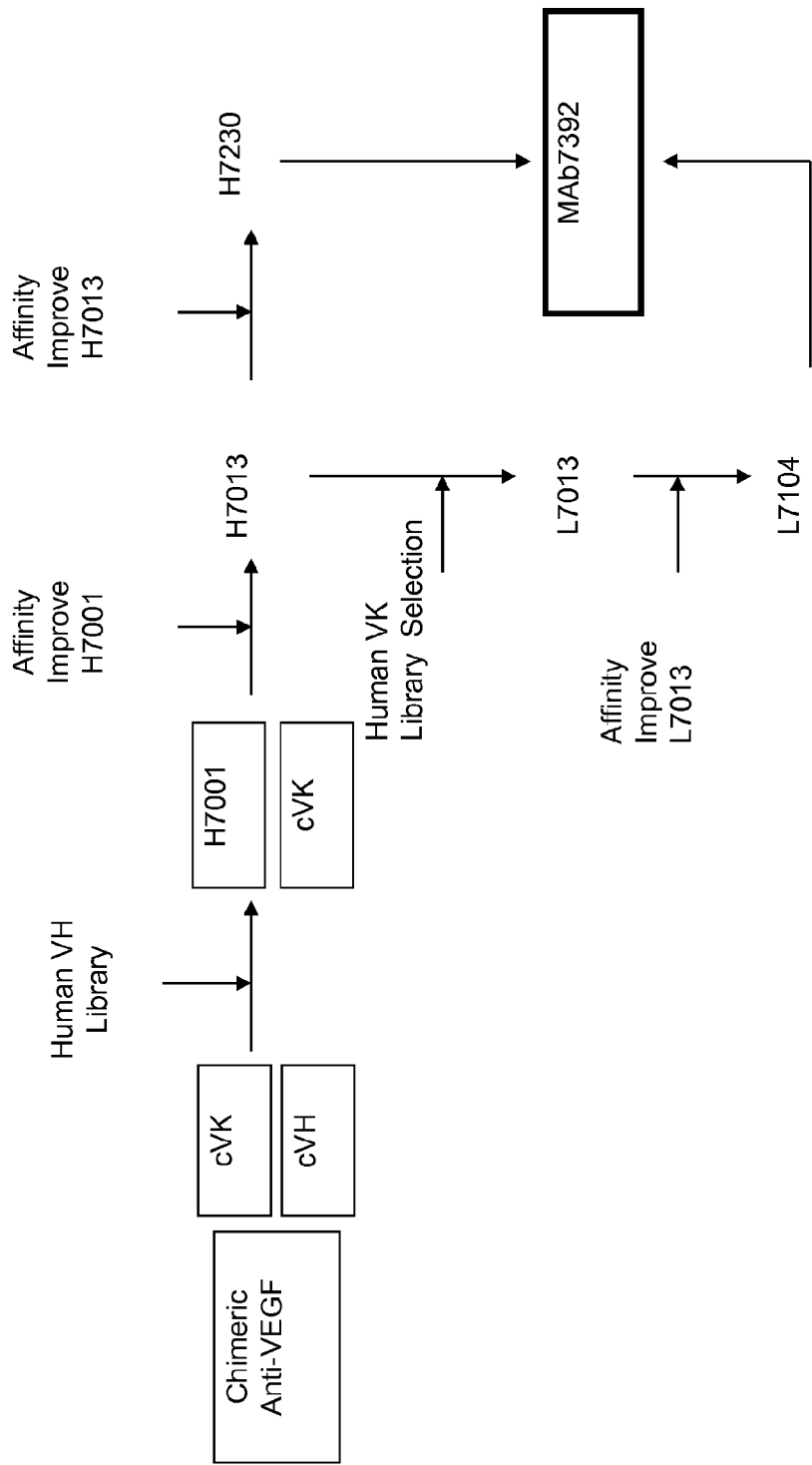
Figure 1. Selection of VEGF Specific Antibodies

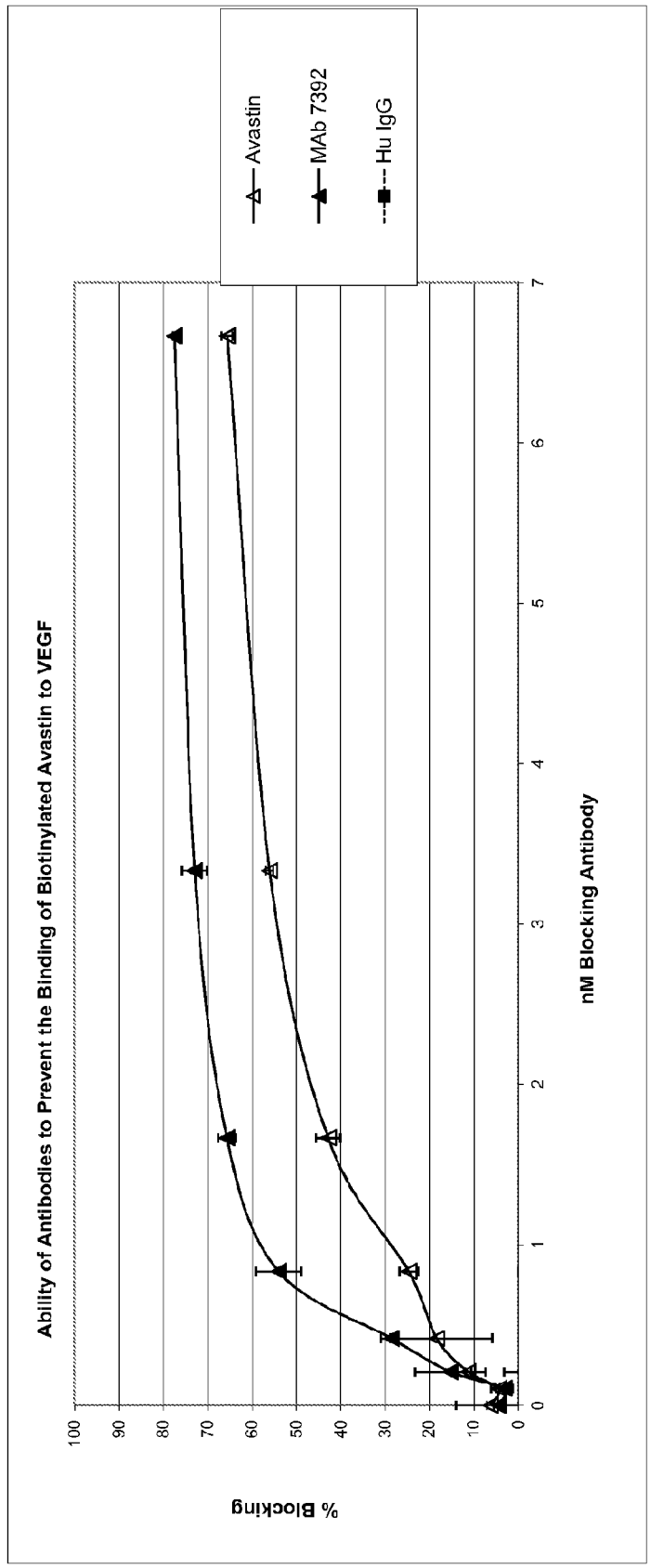
Figure 2: Epitope Blocking Data

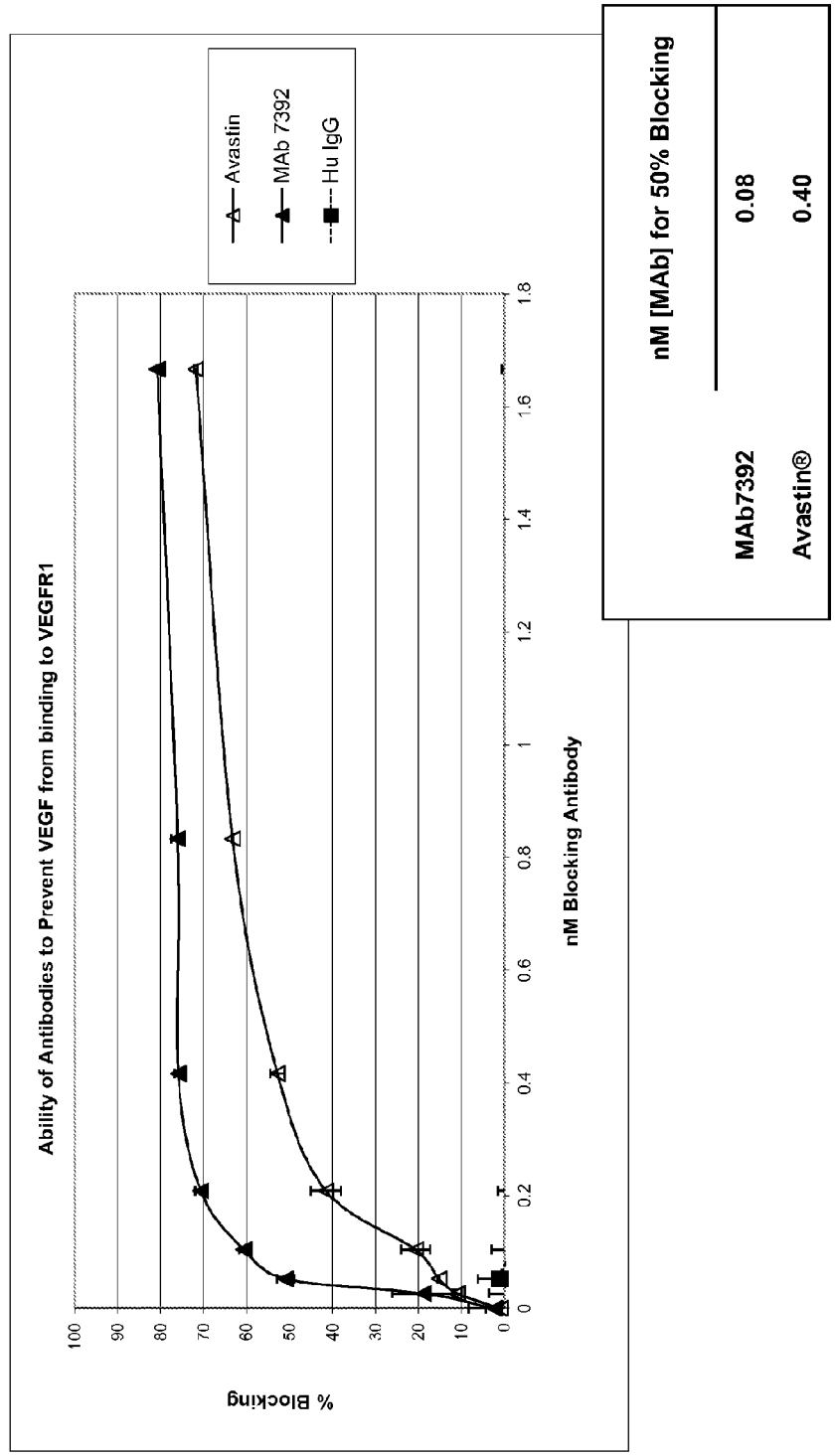
Figure 3: VEGFR1 Blocking

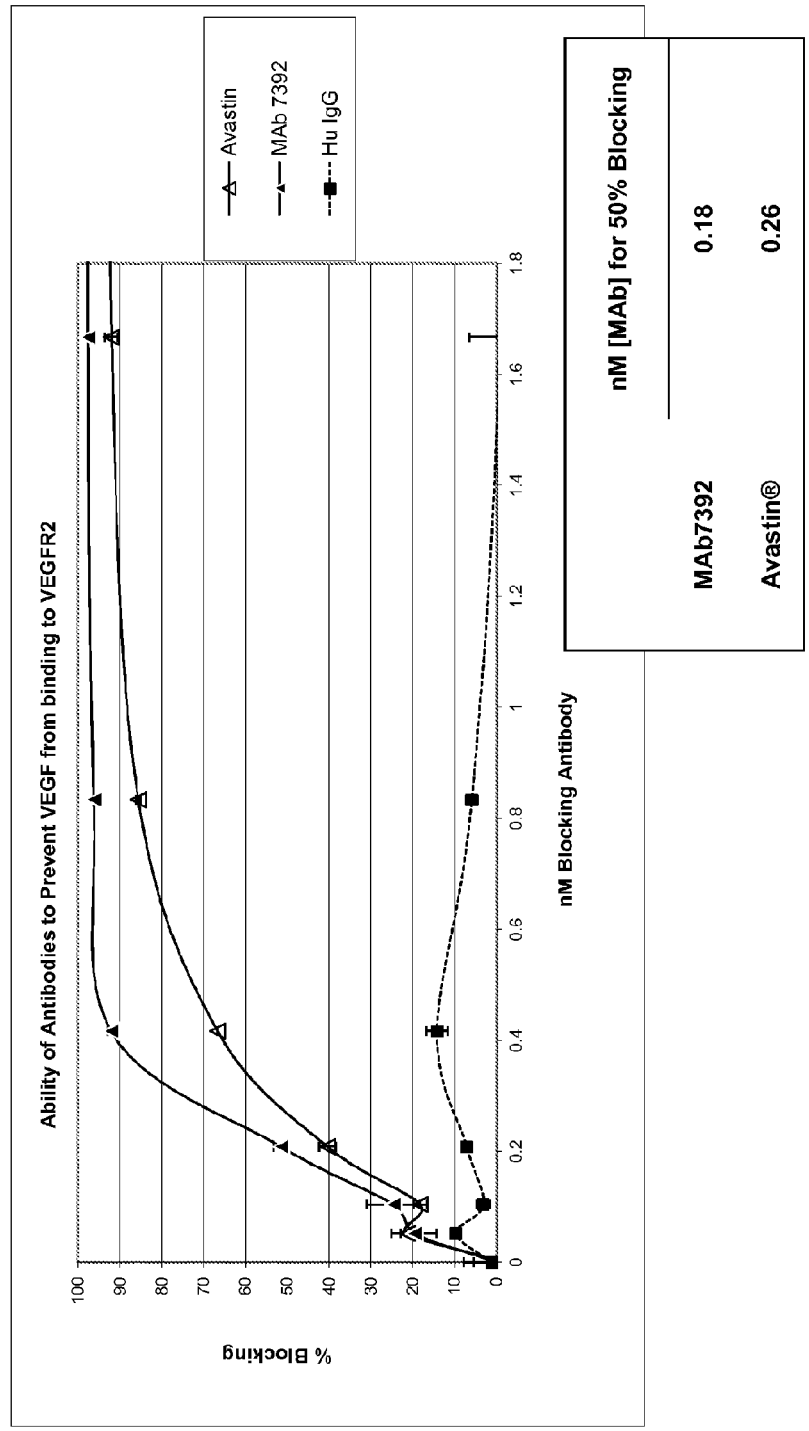
Figure 4: VEGFR2 Blocking

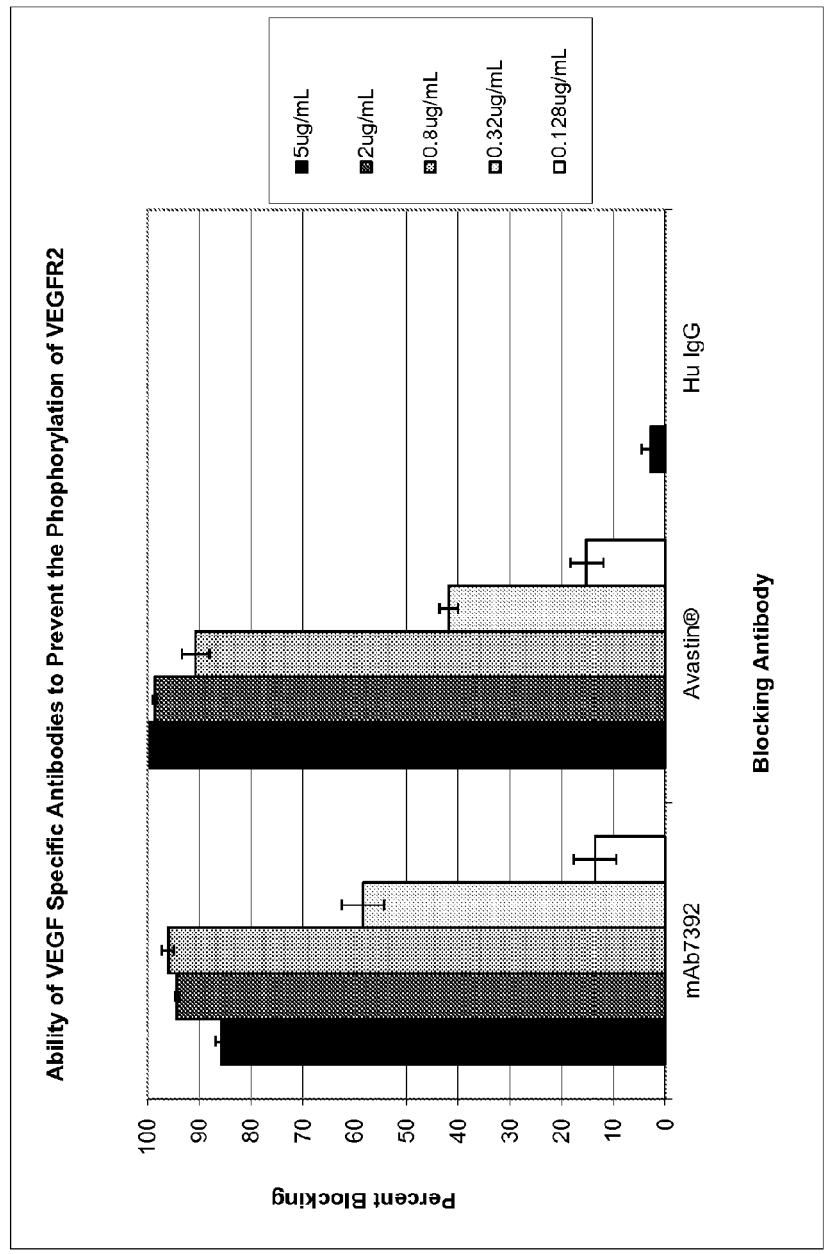
Figure 5: VEGFR2 Phosphorylation Assay

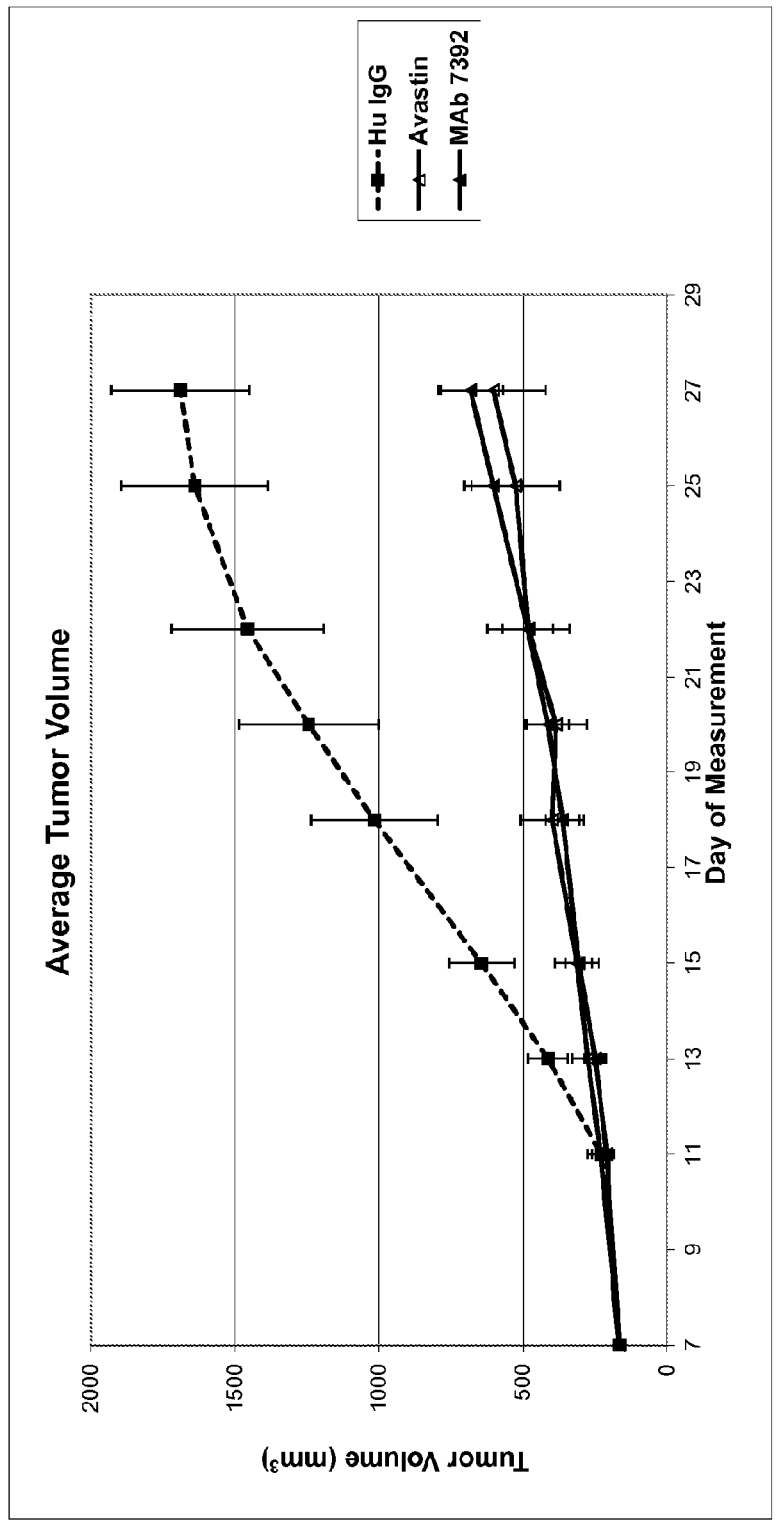
Figure 6: Treatment of Established Xenografts

ANTI-VEGF ANTIBODIES AND USES THEREOF

CROSS REFERENCE TO RELATED APPLICATIONS

This application is a U.S. National Stage Application based on PCT/US2011/040361, filed Jun. 14, 2011, which claims the benefit of U.S. Provisional Application No. 61/354,590, filed on Jun. 14, 2010, all of which are herein incorporated by reference in their entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 427451SEQLIST.TXT, created on Dec. 10, 2012, and having a size of 6 kilobytes, and was filed in the Preliminary Amendment filed on Dec. 13, 2012. The sequence listing contained in this ASCII formatted document is part of the specification and is herein incorporated by reference in its entirety.

BACKGROUND OF THE INVENTION

1. Field of the Invention

The invention relates to a novel anti-VEGF antibody, methods of using the antibody, in particular methods for treatment of conditions and diseases associated with VEGF-expression, such as cancer.

2. Background Information

It is well established that vascular endothelial growth factor (VEGF) and its receptors are key regulators of new blood vessel formation, or angiogenesis. The VEGF gene family has several members, including VEGF-A (also referred to herein as "VEGF"), VEGF-B, VEGF-C, VEGF-D, VEGF-E, and P1GF. See, Ho and Kuo, *Int. J. Biochem Cell Biol.* 2007; 39 (7-8): 1349-1357. There are numerous alternatively spliced isoforms of human VEGF, including $VEGF_{165}$, $VEGF_{121}$, $VEGF_{189}$, and $VEGF_{206}$. See, Ho and Kuo, *Int. J. Biochem Cell Biol.* 2007; 39 (7-8): 1349-1357; Ferrara et al., *Nature Med.* 2003; 9 (6):669-676. The $VEGF_{165}$ isoform is the most prevalent and mitogenic and is most similar in properties to the 45 kDa native VEGF. See, Ho and Kuo, *Int. J. Biochem Cell Biol.* 2007; 39 (7-8): 1349-1357; Ferrara et al., *Nature Med.* 2003; 9 (6):669-676.

VEGF exists a 45 kD homodimeric glycoprotein which binds to two related tyrosine kinase receptors. Ferrara et al., *Nature Med.* 2003; 9 (6):669-676. VEGFR-1 (also known as Flt-1), is a high affinity receptor for VEGF whose function is not fully understood. VEGFR-2 (also known as KDR or Flk1), is the other high affinity receptor for VEGF, and is the receptor through which the pro-angiogeneic activity of VEGF is believed to occur. See Ferrara et al., *Nature Med.* 2003; 9 (6):669-676. VEGFR2 forms a dimer and autophosphorylates when bound to VEGF. Dougher and Terman, *Oncogene.* 1999; 18: 1619-1627. This, in turn, activates several signaling cascades that promote endothelial cell growth and migration, and which ultimately lead to angiogenesis. See Hicklin and Ellis, *J. Clin. Oncol.* 2005; 23 (5): 1011-1027.

During embryonic and postnatal development, VEGF participates in angiogenesis, vasculogenesis, and lymphangiogenesis. VEGF has also been found to play a role in adult processes, as well, including ovarian angiogenesis, endochondral bone formation, tissue regeneration, survival of hematopoietic stem cells, and regulation of erythropoietin. See, Ho and Kuo, *Int. J. Biochem Cell Biol.* 2007; 39 (7-8): 1349-1357. It is the involvement of VEGF in disease processes such as cancer and other neoplastic conditions, inflammatory disease, ocular disease, and ischemic disease that makes it a target for treatment.

Angiogenesis is a requirement for a tumor to grow beyond 1 to 2 mm. The formation of new vasculature is a result of the tumor environment "switching" on several pathways that promote tumor angiogenesis. Inhibition of VEGF-induced angiogenesis by a monoclonal antibody that specifically binds to VEGF was shown to suppress tumor growth in vivo. See Kim et al., *Nature* 1993; 362: 841-844, which ultimately led to the development of therapeutic antibody, bevacizumab. However, bevacizumab is a humanized version of a mouse antibody. Humanized antibodies have an increased risk of immunogenicity when introduced into the human body because they retain significant portions of a mouse protein that is recognized as foreign. Also, humanization of an antibody can lead to decreased affinity for the target protein, rendering it less effective. Accordingly, there exists a need for an anti-VEGF antibody that is generated from human sequence's and which has improved affinity for the VEGF protein.

BRIEF SUMMARY OF THE INVENTION

The invention relates to a novel anti-VEGF antibody, methods of using the antibody, in particular methods for treatment of conditions and diseases associated with VEGF-expression, such as cancer.

In one embodiment, the invention is directed to an isolated antibody or antigen binding fragment thereof that specifically binds to VEGF, wherein the VH of the antibody or fragment thereof comprises a Kabat heavy chain complementarity determining region-3 (VH-CDR3) amino acid sequence identical to SEQ ID NO:5 and the isolated antibody or antigen binding fragment thereof comprises at least one CDR selected from the group consisting of: a Chothia-Kabat heavy chain complementarity determining region-1 (VH-CDR1) amino acid sequence identical SEQ ID NO:3, a Kabat heavy chain complementarity determining region-2 (VH-CDR2) amino acid sequence identical SEQ ID NO:4, a Kabat light chain complementarity determining region-1 (VL-CDR1) amino acid sequence identical to SEQ ID NO:6, a Kabat light chain complementarity determining region-2 (VL-CDR2) amino acid sequence identical to SEQ ID NO:7, a Kabat light chain complementarity determining region-3 (VL-CDR3) amino acid sequence identical to SEQ ID NO:8, and a combination of 2 or more of said CDRs.

In one embodiment, the at least one CDR is a Chothia-Kabat heavy chain complementarity determining region-1 (VH-CDR1) amino acid sequence identical SEQ ID NO:3. In another embodiment, the at least one CDR is a Kabat heavy chain complementarity determining region-2 (VH-CDR2) amino acid sequence identical SEQ ID NO:4. In another embodiment, the at least one CDR is a Kabat light chain complementarity determining region-1 (VL-CDR1) amino acid sequence identical to SEQ ID NO:6. In another embodiment, the at least one CDR is a Kabat light chain complementarity determining region-2 (VL-CDR2) amino acid sequence identical to SEQ ID NO:7. In another embodiment, the at least one CDR is a Kabat light chain complementarity determining region-3 (VL-CDR3) amino acid sequence identical to SEQ ID NO:8.

In another embodiment, the invention is directed to an isolated antibody or antigen-binding fragment thereof that specifically binds to VEGF, wherein the VH of the antibody or fragment thereof comprises VH-CDR1, VH-CDR2, and VH-CDR3 amino acid sequences comprising SEQ ID NOs: 3, 4, and 5, respectively.

In another embodiment, the invention is directed to an isolated antibody or antigen-binding fragment thereof that specifically binds to VEGF, wherein the VL of the antibody or fragment thereof comprises VL-CDR1, VL-CDR2, and VL-CDR3 amino acid sequences comprising SEQ ID NOs: 6, 7, and 8, respectively.

In a particular embodiment, the antibody or fragment thereof according to the invention comprises VH framework regions that are identical to the VH framework regions of SEQ ID NO:1, except for five or fewer amino acid substitutions. In a more specific embodiment, the VH framework regions are identical to the VH framework regions of SEQ ID NO: 1. In another particular embodiment, the antibody or fragment thereof according to the invention comprises VL framework regions that are identical to the VL framework regions of SEQ ID NO:2, except for five or fewer amino acid substitutions. In a more specific embodiment, the VL framework regions are identical to the VL framework regions of SEQ ID NO:1.

In one embodiment, the VH of the antibody or fragment thereof comprises the amino acid sequence of SEQ ID NO: 1. In another embodiment, the VL of the anti-VEGF antibody or fragment thereof comprises the amino acid sequence of SEQ ID NO:2. In one embodiment, the VH and VL of the anti-VEGF antibody or fragment thereof comprise amino acid sequences identical to SEQ ID NO:1 and SEQ ID NO:2, respectively. In one embodiment, the anti-VEGF antibody is MAb 7392 or an antigen-binding fragment thereof.

In certain embodiments, the anti-VEGF antibody or fragment thereof as described above specifically binds to a VEGF polypeptide or fragment thereof, or a VEGF variant polypeptide with an affinity characterized by a dissociation constant ($K_D$) less than about $3.5 \times 10^{-9}$ M, $3.9 \times 10^{-9}$ M, $5 \times 10^{-9}$ M, $10^{-9}$ M, $5 \times 10^{-10}$ M, $9.1 \times 10^{-10}$ M, or $10^{-10}$ M. In a particular embodiment, the VEGF polypeptide or fragment thereof, or a VEGF variant polypeptide is human and the $K_D$ is about $3.5 \times 10^{-9}$ M to about $10 \times 10^{-10}$ M. In a more specific embodiment, the $K_D$ is about $9.1 \times 10^{-10}$ M. In one embodiment, the anti-VEGF antibody or fragment thereof competitively inhibits reference monoclonal antibody MAb 7392 from specifically binding to VEGF.

In certain embodiments, the anti-VEGF antibody or fragment thereof is selected from the group consisting of an Fab fragment, an F(ab)$_2$ fragment, an Fv fragment, and a single chain antibody.

In one embodiment, the anti-VEGF antibody or fragment thereof comprises a light chain constant region selected from the group consisting of a human kappa constant region and a human lambda constant region. In another embodiment, the anti-VEGF antibody or fragment thereof comprises a heavy chain constant region or fragment thereof. In certain embodiments, the heavy chain constant region or fragment thereof is human IgG1, IgG2, IgG3, IgG4, IgM, IgA1, IgA2, IgE or IgD.

In one embodiment, the antibody or fragment thereof inhibits VEGF from binding to a VEGF receptor. In a more specific embodiment, the VEGF receptor is selected from the group consisting of VEGFR1 and VEGFR2. In another embodiment, the anti-VEGF antibody or fragment thereof inhibits phosphorylation of VEGFR2 by VEGF.

In one embodiment, the anti-VEGF antibody or fragment thereof as described above, comprises only one murine CDR. In a more specific embodiment, the murine CDR is VH-CDR3. In a more specific embodiment, the VH-CDR3 is SEQ ID NO:5.

In one embodiment, the anti-VEGF antibody or fragment thereof further comprises a heterologous polypeptide fused thereto. In another embodiment, the anti-VEGF antibody or fragment thereof is conjugated to an agent selected from the group consisting of a cytotoxic agent, a therapeutic agent, a cytostatic agent, a biological toxin, a prodrug, a peptide, a protein, an enzyme, a virus, a lipid, a biological response modifier, a pharmaceutical agent, a lymphokine, a heterologous antibody or fragment thereof, a detectable label, polyethylene glycol (PEG), and a combination of two or more of any said agents. In a more specific embodiment, the cytotoxic agent is selected from the group consisting of a radionuclide, a biotoxin, an enzymatically active toxin, or a combination of two or more of any said cytotoxic agents. In another embodiment, the anti-VEGF antibody or fragment thereof comprises a detectable label selected from the group consisting of an enzyme, a fluorescent label, a chemiluminescent label, a bioluminescent label, a radioactive label, or a combination of two or more of any said detectable labels.

In one aspect, the invention is directed to composition comprising the anti-VEGF antibody or fragment thereof and a carrier.

In another aspect, the invention is also directed to isolated polynucleotides encoding polypeptides of anti-VEGF antibodies or fragments thereof. In one embodiment, the invention is directed to an isolated polynucleotide comprising a nucleic acid that encodes an antibody VH polypeptide, wherein the amino acid sequence of the VH polypeptide is identical to SEQ ID NO:1; wherein an antibody or antigen binding fragment thereof comprising the VH polypeptide specifically binds to VEGF. In a specific embodiment, the nucleic acid comprises a nucleotide sequence comprising SEQ ID NO:9. In another specific embodiment, the nucleic acid comprises a nucleotide sequence consisting of SEQ ID NO:9.

In another embodiment, the invention is directed to an isolated polynucleotide comprising a nucleic acid that encodes an antibody VL polypeptide, wherein the amino acid sequence of the VL polypeptide is identical to SEQ ID NO:2; and wherein an antibody or antigen binding fragment thereof comprising the VL polypeptide specifically binds to VEGF. In a specific embodiment, the nucleic acid comprises a nucleotide sequence comprising SEQ ID NO:10. In another specific embodiment, the nucleic acid comprises a nucleotide sequence consisting of SEQ ID NO:10.

In one embodiment, the invention is directed to an isolated polynucleotide comprising a nucleic acid that encodes an antibody VH polypeptide, wherein the amino acid sequence of the VH polypeptide is identical to SEQ ID NO:1, except for five or fewer substitutions in the framework region; wherein an antibody or antigen binding fragment thereof comprising said VH polypeptide specifically binds to VEGF.

In another embodiment, the invention is directed to an isolated polynucleotide comprising a nucleic acid that encodes an antibody VL polypeptide, wherein the amino acid sequence of said VL polypeptide is identical to SEQ ID NO:2, except for five or fewer substitutions in the framework region; wherein an antibody or antigen binding fragment thereof comprising said VL polypeptide specifically binds to VEGF.

In one embodiment, the invention is directed to an isolated polynucleotide comprising a nucleic acid that encodes a VH-CDR3 amino acid sequence identical to SEQ ID NO:5 and a nucleic acid that encodes at least one additional amino acid sequence selected from the group consisting of a VH-CDR1 amino acid sequence identical to SEQ ID NO:3; a VH-CDR2 amino acid sequence identical to SEQ ID NO:4, and a combination thereof, wherein an antibody or antigen binding fragment thereof comprising a VH encoded by the polynucleotide specifically binds to VEGF.

In another embodiment, the invention is directed to an isolated polynucleotide comprising a nucleic acid that encodes a VH-CDR3 amino acid sequence identical to SEQ ID NO:5 and a nucleic acid that encodes a VH-CDR1 amino acid sequence identical to SEQ ID NO:3; wherein an antibody or antigen binding fragment thereof comprising a VH encoded by said polynucleotide specifically binds to VEGF.

In another embodiment, the invention is directed to an isolated polynucleotide comprising a nucleic acid that encodes a VH-CDR3 amino acid sequence identical to SEQ ID NO:5 and a nucleic acid that encodes a VH-CDR2 amino acid sequence identical to SEQ ID NO:4; and wherein an antibody or antigen binding fragment thereof comprising a VH encoded by said polynucleotide specifically binds to VEGF.

In one embodiment, the invention is directed to an isolated polynucleotide comprising a nucleic acid that encodes at least one VL-CDR amino acid sequence identical to a sequence selected from the group consisting of SEQ ID NO:6; SEQ ID NO:7, SEQ ID NO:8, and a combination of 2 or more of said VL-CDR amino acid sequences, wherein an antibody or antigen binding fragment thereof comprising a VL encoded by the polynucleotide specifically binds to VEGF.

In another embodiment, the invention is directed to an isolated polynucleotide comprising a nucleic acid that encodes a VL-CDR1 amino acid sequence identical to SEQ ID NO:6; wherein an antibody or antigen binding fragment thereof comprising a VL encoded by said polynucleotide specifically binds to VEGF.

In another embodiment, the invention is directed to an isolated polynucleotide comprising a nucleic acid that encodes a VL-CDR2 amino acid sequence identical to SEQ ID NO:7; wherein an antibody or antigen binding fragment thereof comprising a VL encoded by said polynucleotide specifically binds to VEGF.

In another embodiment, the invention is directed to an isolated polynucleotide comprising a nucleic acid that encodes a VL-CDR3 amino acid sequence identical to SEQ ID NO:8; and wherein an antibody or antigen binding fragment thereof comprising a VL encoded by said polynucleotide specifically binds to VEGF.

In another embodiment, the invention is directed to an isolated polynucleotide comprising a nucleic acid that encodes an antibody VH polypeptide, wherein the VH polypeptide comprises VH-CDR1, VH-CDR2, and VH-CDR3 amino acid sequences comprising SEQ ID NOs: 3, 4, and 4, respectively; wherein an antibody or antigen binding fragment thereof comprising said polypeptide specifically binds to VEGF.

In another embodiment, the invention is directed to an isolated polynucleotide comprising a nucleic acid that encodes an antibody VL polypeptide, wherein the VL polypeptide comprises VL-CDR1, VL-CDR2, and VL-CDR3 amino acid sequences comprising SEQ ID NOs: 6, 7, and 8, respectively; and wherein an antibody or antigen binding fragment thereof comprising said polypeptide specifically binds to VEGF.

In certain embodiments, the polynucleotide further comprises a nucleic acid encoding a signal peptide fused to the antibody VH polypeptide. In certain embodiments, the polynucleotide further comprises a nucleic acid encoding a signal peptide fused to the antibody VL polypeptide. In a particular embodiment, the polynucleotide further comprises a nucleic acid encoding a heavy chain constant region CH1 domain fused to the antibody VH polypeptide. In a particular embodiment, the polynucleotide further comprises a nucleic acid encoding a heavy chain constant region CH2 domain fused to the antibody VH polypeptide. In a particular embodiment, the polynucleotide further comprises a nucleic acid encoding a heavy chain constant region CH3 domain fused to said VH polypeptide. In a particular embodiment, the polynucleotide further comprises a nucleic acid encoding a heavy chain hinge region fused to the VH polypeptide. In a more particular embodiment, the heavy chain constant region is human IgG1, IgG2, IgG3, IgG4, IgM, IgA1, IgA2, IgE or IgD. In a particular embodiment, the polynucleotide further comprises a nucleic acid encoding a light chain constant region domain fused to the VL polypeptide. In a more particular embodiment, the light chain constant region is human kappa or human lambda.

In another aspect, the invention is directed to a vector comprising the above polynucleotides. In certain embodiments, the polynucleotide is operably associated with a promoter. In another aspect, the invention is directed to a host cell comprising the vector; a method of producing an antibody or fragment thereof that specifically binds VEGF, comprising culturing the host cell and recovering the antibody, or fragment thereof; and isolated polypeptide produced by the method.

In another aspect, the invention is directed to n isolated polypeptide encoded by the polynucleotides and/or an isolated antibody or fragment thereof comprising the polypeptide encoded by the polynucleotides.

In another aspect, the invention is directed to compositions. In one embodiment, the invention is directed to a composition comprising an isolated VH encoding polynucleotide and an isolated VL encoding polynucleotide, wherein said VH encoding polynucleotide and said VL encoding polynucleotide comprise nucleic acids encoding the amino acid sequences of SEQ ID NO:1 and SEQ ID NO: 2, respectively; and wherein an antibody or fragment thereof encoded by said VH and VL encoding polynucleotides specifically binds VEGF.

In another embodiment, the invention is directed to a composition comprising an isolated VH encoding polynucleotide and an isolated VL encoding polynucleotide, wherein the VH encoding polynucleotide encodes a VH polypeptide comprising VH-CDR1, VH-CDR2, and VH-CDR3 amino acid sequences consisting of SEQ ID NOs: 3, 4, and 5, respectively; wherein the VL encoding polynucleotide encodes a VL polypeptide comprising VL-CDR1, VL-CDR2, and VL-CDR3 amino acid sequences consisting of SEQ ID NOs: 6, 7, and 8, respectively; and wherein an antibody or fragment thereof encoded by the VH and VL encoding polynucleotides specifically binds VEGF.

In a particular embodiment, the VH encoding polynucleotide further comprises a nucleic acid encoding a signal peptide fused to the antibody VH polypeptide. In another particular embodiment, the VL encoding polynucleotide further comprises a nucleic acid encoding a signal peptide fused to the antibody VL polypeptide. In another particular embodiment, the VH encoding polynucleotide further comprises a nucleic acid encoding a heavy chain constant region CH1 domain fused to the VH polypeptide. In another particular embodiment, the VH encoding polynucleotide further comprises a nucleic acid encoding a heavy chain constant region CH2 domain fused to said VH polypeptide. In another particular embodiment, the VH encoding polynucleotide further comprises a nucleic acid encoding a heavy chain constant region CH3 domain fused to the VH polypeptide. In another particular embodiment, the VH encoding polynucleotide further comprises a nucleic acid encoding a heavy chain hinge region fused to the VH polypeptide. In a more particular embodiment, the heavy chain constant region is human IgG1, IgG2, IgG3, IgG4, IgM, IgA2, IgE or IgD. In another embodiment, the VL encoding polynucleotide further comprises a nucleic acid encoding a light chain constant region domain fused to said VL polypeptide. In a particular embodiment, the light chain constant region is human kappa or human lambda.

In a particular embodiment, the VH encoding polynucleotide and the VL encoding polynucleotide are contained on a single vector. In another embodiment, the VH encoding polynucleotide is contained on a first vector and the VL encoding polynucleotide is contained on a second vector which is non-identical to the first vector.

In one embodiment, the VH encoding polynucleotide is operably associated with a first promoter and the VL encoding polynucleotide is operably associated with a second promoter. In a particular embodiment, the first and second promoters are copies of the same promoter. In another embodiment, the first and second promoters non-identical. In one embodiment, the first vector and the second vector are contained in a single host cell. In another embodiment, the first vector and the second vector are contained in separate host cells.

In one embodiment, the VH encoding polynucleotide and said VL encoding polynucleotide are fused in frame in a vector, are co-transcribed from a single promoter operably associated therewith, and are cotranslated into a single chain antibody or antigen-binding fragment thereof. In one embodiment, the VH encoding polynucleotide and the VL encoding polynucleotide are co-transcribed from a single promoter operably associated therewith, but are separately translated. In one embodiment, the vector further comprises an IRES sequence disposed between the VH encoding polynucleotide and the VL encoding polynucleotide. In one embodiment, the polynucleotide encoding a VH and the polynucleotide encoding a VL are separately transcribed, each being operably associated with a separate promoter.

In one aspect, the invention is also directed to methods of using the anti-VEGF antibody or fragment thereof. In one embodiment, the invention is directed to Aa method for neutralizing VEGF in an animal, said method comprising administering to said animal a composition comprising: the isolated anti-VEGF antibody or fragment thereof of the invention; and a pharmaceutically acceptable carrier.

In another embodiment, the invention is directed to a method for treating a cancer in an animal in need of treatment, said method comprising administering to said animal a composition comprising: the isolated anti-VEGF antibody or fragment thereof of the invention; and a pharmaceutically acceptable carrier.

In another embodiment, the invention is directed to method for inhibiting angiogenesis in an animal in need of treatment for cancer, said method comprising administering to said animal a composition comprising: the isolated anti-VEGF antibody or fragment thereof of the invention; and a pharmaceutically acceptable carrier.

In a particular embodiment, the cancer is a solid tumor, more particularly, a cancer selected from the group consisting of colorectal cancer, lung cancer, renal cell carcinoma, breast cancer, non-small cell lung cancer, and glioblastoma. In one embodiment, the cancer is metastatic. In another embodiment, the cancer is non-resectable.

In another aspect, the method further comprises administering to the animal at least one additional therapy. In one embodiment, the at least one additional therapy is selected from the group consisting of radiation therapy and chemotherapy. In another embodiment, the at least one additional therapy is a chemotherapy is selected from the group consisting of taxane, paclitaxel, carboplatin, 5-fluorouracil, leucovorin, capecitabine, oxaliplatin, irinotecan, or any combination thereof.

In a particular embodiment, the animal is a mammal. In a more specific embodiment, the mammal is a human.

BRIEF DESCRIPTION OF THE DRAWINGS/FIGURES

FIG. 1. Selection of VEGF-Specific Antibodies. Illustrated in FIG. 1 is a flow chart depicting the antibody selection process. "cVK" refers to the chimeric anti-VEGF kappa light chain variable region. "cVH" refers to the chimeric anti-VEGF heavy chain variable region.

FIG. 2. Epitope Blocking Assay. This figure compares the ability of MAb 7392, bevacizumab ("Avastin"), and human IgG ("Hu IgG", negative control) to prevent the binding of biotinylated bevacizumab to VEGF.

FIG. 3. VEGFR1 Blocking. This figure compares the ability of MAb 7392, bevacizumab ("Avastin"), and human IgG ("Hu IgG", negative control) to prevent VEGF from binding to its receptor, VEGFR1.

FIG. 4. VEGFR2 Blocking. This figure compares the ability of MAb 7392, bevacizumab ("Avastin"), and human IgG ("Hu IgG", negative control) to prevent VEGF from binding to its receptor, VEGFR2.

FIG. 5. VEGFR2 Phosphorylation Assay. This figure compares the ability of MAb 7392, bevacizumab ("Avastin"), and human IgG ("Hu IgG", negative control) to prevent phosphorylation of VEGFR2 by VEGF.

FIG. 6. Treatment of Established Xenografts. This figure compares the effects of treatment with MAb 7392, bevacizumab ("Avastin"), and human IgG ("Hu IgG", negative control) on tumor volume in mouse xenograft models that had been injected intraperitoneally with A673 human rhabdomyosarcoma cells.

DETAILED DESCRIPTION OF THE INVENTION

I. Definitions

It is to be noted that the term "a" or "an" entity refers to one or more of that entity; for example, "an anti-VEGF antibody" is understood to represent one or more anti-VEGF antibodies. As such, the terms "a" (or "an"), "one or more," and "at least one" can be used interchangeably herein.

As used herein, the term "tumor" refers to all neoplastic cell growth and proliferation, whether malignant or benign, and all cancerous and pre-cancerous cells and tissues.

"Invasive angiogenesis" refers to the formation of blood vessels for the support of pathological conditions, including malignant and non-malignant tumors as well as the abnormal formation of new blood vessels in macular degeneration.

The terms, "cancer" and "cancerous" refer to or describe the physiological condition in mammals that is typically characterized by unregulated cell growth. Examples of cancer include but are not limited to carcinomas, lymphomas and leukemias.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-VEGF antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-VEGF antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs." As used herein a "derivative" of an anti-VEGF antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Derivatives of anti-VEGF antibodies and antibody polypeptides of the present invention, may include polypeptides that have been altered so as to exhibit additional features not found on the reference antibody or antibody polypeptide of the invention.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-VEGF binding molecule, e.g., an antibody or antigen binding fragment thereof, contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an anti-VEGF antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" or "antigen binding molecule" of the present invention refers in its broadest sense to a molecule that specifically binds an antigenic determinant. In one embodiment, the binding molecule specifically binds to native VEGF ("VEGF-A"), e.g., a 45 kDa homodimeric glycoprotein, or other allelic or variant forms of VEGF. In another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, an a binding molecule of the invention comprises at least five CDRs from one or more antibody molecules. In another embodiment, a binding molecule of the invention comprises at least six CDRs from one or more antibody molecules.

The present invention is directed to certain anti-VEGF antibodies, or antigen-binding fragments, variants, or derivatives thereof. Unless specifically referring to full-sized antibodies such as naturally occurring antibodies, the term "anti-VEGF antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s). In certain embodiments, a "human" antibody as described herein may include one murine CDR, e.g., a murine VH-CDR3.

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a VEGF polypeptide or fragment or variant thereof. Standard techniques known to those of skill in the art can be used to introduce mutations in the nucleotide sequence encoding a human anti-VEGF antibody, including, but not limited to, site-directed mutagenesis and PCR-mediated mutagenesis which result in amino acid substitutions. Preferably, the variants (including derivatives) encode less than 5 amino acid substitutions, less than 4 amino acid substitutions, less than 3 amino acid substitutions, or less than 2 amino acid substitutions relative to the reference VH region framework or the VL region framework. In certain embodiments, the amino acid substitutions are conservative amino acid substitution, discussed further below.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) ANTIBODIES: A LABORATORY MANUAL (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, γ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementary determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-VEGF antibody or antigen-binding fragment, variant, or derivative thereof of the present invention are according to the Kabat numbering system. It is noted that sequences presented in the accompanying SEQUENCE LISTING are not numbered according to Kabat, but it is well within the ordinary skill in the art to determine the Kabat numbering of sequences in the SEQUENCE LISTING.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-VEGF antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

The heavy chain portions of a binding molecule for use in the diagnostic and treatment methods disclosed herein may be derived from different immunoglobulin molecules. For example, a heavy chain portion of a polypeptide may comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-VEGF antibodies, or antigen-binding fragments, variants, or derivatives thereof disclosed herein may be described or specified in terms of the epitope(s) or portion(s) of an antigen, e.g., a target polypeptide disclosed herein (e.g., VEGF) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-VEGF antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of VEGF.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first epitope preferentially if it binds the first epitope with an off rate (k(off)) that is less than the antibody's k(off) for the second epitope.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays.

As used herein, the term "affinity" refers to a measure of the strength of the binding of an individual epitope with the CDR of an immunoglobulin molecule. See, e.g., Harlow et al. (1988) ANTIBODIES: A LABORATORY MANUAL (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-VEGF binding molecules, e.g., antibodies or antigen-binding fragments, variants or derivatives thereof, of the invention may also be described or specified in terms of their binding affinity to a polypeptide of the invention, e.g., VEGF, more specifically, human VEGF (also known as "VEGF-A"). Preferred binding affinities include those with a dissociation constant or Kd less than about $3.9 \times 10^{-9}$ more preferably, less than or equal to about $9.1 \times 10^{-10}$ M (0.91 nM). In certain embodiments, the anti-VEGF binding molecule, e.g., an antibody or antigen binding fragment thereof, of the invention binds human VEGF with a Kd of about $3.0 \times 10^{-9}$ M to about $10 \times 10^{-10}$ M. In another embodiment, the anti-VEGF binding molecule, e.g., an antibody or antigen binding fragment thereof, of the invention binds human VEGF with a Kd of about $9.1 \times 10^{-9}$ M.

As used herein the term "valency" refers to the number of potential binding domains, e.g., antigen binding domains present in a binding polypeptide or VEGF binding molecule, e.g., an antibody or antigen binding fragment thereof. Each binding domain specifically binds one epitope.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et at, *J. Immunol.* 161:4083 (1998)).

As used herein the term "disulfide bond" includes the covalent bond formed between two sulfa atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" refers to any antibody wherein the antigen binding region or site (e.g., the variable region) is obtained or derived from a first species and the constant region (which may be intact, partial or modified in accordance with the instant invention) is obtained from a second species As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging, survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of an anti-VEGF antibody" and "an animal in need of treatment" includes subjects, such as mammalian subjects, that would benefit from administration of an anti-VEGF antibody used, e.g., for detection of a VEGF polypeptide (e.g., for a diagnostic procedure) and/or from treatment, i.e., palliation or prevention of a disease, with an anti-VEGF antibody. As described in more detail herein, an anti-VEGF antibody can be used in unconjugated form or can be conjugated, e.g., to a drag, prodrug, or an isotope.

II. Target Polypeptide Description

As used herein, the terms "VEGF" and "VEGF polypeptide" are used interchangably. In certain embodiments, VEGF is secreted by a cell. In another embodiment, VEGF is membrane-bound or bound to the extracellular matrix. In another embodiment, VEGF is soluble. In other embodiments, VEGF may include a full-sized VEGF polylpeptide or a fragment thereof, or a VEGF variant polypeptide (including VEGF isoforms and splice variants), wherein the fragment of VEGF or VEGF variant polypeptide retains some or all functional properties of the full-sized, native VEGF.

The full-sized, native human VEGF protein is a homodimeric glycoprotein consisting of two identical 23 kDa polypeptide subunits. See, Ho and Kuo, *Int. J. Biochem Cell Biol.* 2007; 39 (7-8): 1349-1357. The VEGF gene family has several members, including VEGF-A (also referred to herein as "VEGF"), VEGF-B, VEGF-C, VEGF-D, and P1GF. See, Ho and Kuo, Int. *J. Biochem Cell Biol.* 2007; 39 (7-8): 1349-1357. There are numerous alternatively spliced isoforms of human VEGF, including $VEGF_{165}$, $VEGF_{121}$, $VEGF_{189}$, and $VEGF_{206}$, which have different bioavailabilities, bioactivities, and receptor specificities. See, Ho and Kuo, *Int. J. Biochem Cell Biol.* 2007; 39 (7-8): 1349-1357; Ferrara et al., *Nature Med.* 2003; 9 (6):669-676. The $VEGF_{165}$ isoform is the most prevalent and mitogenic and is most similar in properties to the 45 kDa native VEGF. See, Ho and Kuo, *Int. J. Biochem Cell Biol.* 2007; 39 (7-8): 1349-1357; Ferrara et al., *Nature Med.* 2003; 9 (6):669-676.

VEGF expression and activity is modulated by a number of factors, including hypoxia, mechanical forces, dysregulation of tumor suppressors and oncogenes, inflammatory mediators (e.g., cytokines), and other growth factors. See, Ho and Kuo, *Int. J. Biochem Cell Biol.* 2007; 39 (7-8): 1349-1357. Once expressed, some secreted VEGF is sequestered by the extracellular matrix, which can act as a reservoir that releases VEGF through proteolysis. See, Ho and Kuo, *Int. J. Biochem Cell Biol.* 2007; 39 (7-8): 1349-1357.

VEGF binds two receptor tyrosine kinases with high affinity—VEGFR1 (Flt-1) and VEGFR2 (KDR, Flk1)—which are found mainly on the surface of vascular endothelial cells. Gerber and Ferrara, *Cancer Res.* 2005; 65: 671-680. It is thought that only VEGFR-2 activation induces angiogenesis, mitogenesis, and increased vascular permeability through a process of autophosphorylation that activates downstream signaling pathways such as phosphatidylinositol 3'-OH kinase/Akt. Gerber and Ferrara, *Cancer Res.* 2005; 65: 671-680, VEGFR1 is thought to act as a decoy receptor that suppresses the availability of VEGF to VEGFR2, and may be important in hematopoiesis, matrix metalloproteinase development, and release of growth factors from endothelial cells. Gerber and Ferrara, *Cancer Res.* 2005; 65: 671-680.

Antagonism of VEGF with monoclonal antibodies has been shown to inhibit primary tumor growth, primarily by disrupting the blood supply to tumors and to inhibit tumor metastases. Gerber and Ferrara, *Cancer Res.* 2005; 65: 671-680.

For reviews related to VEGF and VEGF inhibition, see Ferrara, *Nature Reviews* 2002; 2: 795-803; Ho and Kuo, *Int. J. Biochem Cell Biol.* 2007; 39 (7-8): 1349-1357; Ferrara, et al., *Nature Med.* 2003; 9:669-676; Pander et al., *Drug Discovery Today* 2007; 12: 1054-1060; Hicklin and Ellis, *J. Clin. Oncol.* 2005; 5:1011-1027; and Gerber and Ferrara, *Cancer Res.* 2005; 65: 671-680 (each of which is incorporated herein by reference in its entirety).

III. Anti-VEGF Antibodies

Antibodies that bind VEGF have been described the art. See, for example, U.S. Pat. No. 6,884,879 and Presta et al., *Cancer Res.* 57: 4593-4599 (1997), each of which is herein incorporated in its entirety by reference.

The antibodies according to the invention comprise anti-VEGF antibodies or antigen-binding fragments, variants, or derivatives thereof that bind to VEGF, e.g., MAb 7392 as described herein. In certain embodiments the anti-VEGF antibodies bind human VEGF. In other embodiments, the anti-VEGF antibodies block VEGF binding to its receptor, e.g., VEGFR1 or VEGFR2. In certain embodiments, the anti-VEGF antibodies block phosphorylation of VEGFR2 by VEGF.

In one embodiment, the present invention provides an isolated binding molecule, e.g., an antibody or antigen binding fragment thereof, which specifically binds to the same VEGF epitope as MAb7392. In another embodiment, the present invention provides an isolated binding molecule, e.g., an antibody or antigen binding fragment thereof, that specifically binds to VEGF, and competitively inhibits MAb 7392 from specifically binding to VEGF. In certain embodiments, the antibody specifically binds VEGF with an affinity of less than about $3.9 \times 10^{-9}$ M. In another embodiment, the antibody specifically binds VEGF with an affinity of less than about $9.1 \times 10^{-10}$ M.

In one embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is identical to CDR1, CDR2 or CDR3 of SEQ ID NO:1.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is identical to SEQ ID NO: 3, SEQ ID NO: 4, or SEQ ID NO: 5.

In another embodiment, the present invention provides an isolated antibody or antigen-binding fragment thereof comprising, consisting essentially of, or consisting of a VH domain that has an amino acid sequence that is identical to SEQ ID NO:1, wherein an anti-VEGF antibody comprising the encoded VH domain specifically or preferentially binds to VEGF, more specifically, human VEGF.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is identical to CDR1, CDR2 or CDR3 of SEQ ID NO:2.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is identical to SEQ ID NO:6, SEQ ID NO: 7, or SEQ ID NO:8.

In a farther embodiment, the present invention includes an isolated antibody or antigen-binding fragment thereof comprising, consisting essentially of, or consisting of a VL domain that has an amino acid sequence that is identical to SEQ ID NO:2, wherein an anti-VEGF antibody comprising the encoded VL domain specifically or preferentially binds to VEGF.

Polypeptide sequences of the anti-VEGF antibodies or antigen binding molecules thereof including the following:

The H7230 and L7104 variable regions have the following amino acid sequences (CDRs are underlined):

h7230 (SEQ ID NO: 1):
QVQLVQSGAELRKPGASVKISCKASGYSLTYYGMNWVRQAPGQGLEWMG

WINTFTGDSTYAQDFTGRFVFSLDTSVSTAYLQISSLKAEDMAMYYCAK

YPHYYGSSHWYFDVWGQGTTVTVSS

L7104 (SEQ ID NO:2):
EIVLTQSPATLSVSPGERATLSCRASQSVNSNLAWYQQKPGQAPRVLIY

GASTRATGIPARFSGSGSGTEFTLTISSLQSEDFAVYYCQQYSDIPWTF

GQGTKLEIK

The CDRs of MAb 7392 (comprising H7230 and L7104 variable regions) have the following amino acid sequences:

VH-CDR1 (SEQ ID NO: 3):
GYSLTYYGMN

VH-CDR2 (SEQ ID NO: 4):
WINTFTGDSTYAQDFTG

VH-CDR3 (SEQ ID NO: 5):
YPHYYGSSHWYFDV

VL-CDR1 (SEQ ID NO: 6):
RASQSVNSNLA

VL-CDR2 (SEQ ID NO: 7):
GASTRAT

VL-CDR3 (SEQ ID NO: 8):
QQYSDIPWT

Suitable biologically active variants of the anti-VEGF antibodies of the invention can be used in the methods of the present invention. Such variants will retain the desired binding properties of the parent anti-VEGF antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly ↔ Ala, Val↔ Ile↔ Leu, Asp↔ Glu, Lys↔ Arg, Asn ↔ Gln, and Phe↔ Trp↔ Tyr. Modifications are made such that variants continue to possess the desired properties, e.g., being capable of specifically binding to a VEGF, more specifically, human VEGF, e.g., secreted by a cell or attached by a membrane or extracellular matrix component and having VEGF blocking activity, as described herein. Any mutations made in the DNA encoding the variant polypeptide must not place the sequence out of reading frame and preferably will not create complementary regions that could produce secondary mRNA structure. See EP Patent Application Publication No. 75,444.

Methods for measuring anti-VEGF binding molecule, e.g., an antibody or antigen-binding fragment thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167: 4321-4328 (2001); Wang et al., *Blood* 97:3498-3504 (2001); and Giraudon et al., *J Immunol* 172 (2):1246-1255 (2004), all of which are herein incorporated by reference.

The % identity of a polypeptide discussed herein can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Adv. Appl. Math.* 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from a reference anti-VEGF antibody (e.g., MAb 7392, comprising the variable region sequences of SEQ ID NO:1 and SEQ ID NO:2) by 5 or fewer amino acid residues, e.g., in the light or heavy chain framework regions.

The precise chemical structure of a polypeptide capable of specifically binding VEGF and retaining the desired VEGF blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-VEGF antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-VEGF antibody used herein so long as the desired properties of the anti-VEGF antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (e.g., binding specificity for VEGF, binding affinity, and VEGF blocking activity) do not remove the polypeptide sequence from the definition of anti-VEGF antibodies of interest as used herein.

The art provides substantial guidance regarding the preparation and use of polypeptide variants. In preparing the anti-VEGF binding molecule, e.g., an antibody or antigen-binding fragment thereof, variants, one of skill in the art can readily determine which modifications to the native protein's nucleotide or amino acid sequence will result in a variant that is suitable for use as a therapeutically active component of a pharmaceutical composition used in the methods of the present invention.

The constant region of an anti-VEGF antibody may be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-VEGF antibodies, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

Anti-VEGF antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a VEGF polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a VEGF polypeptide) can be determined using techniques described herein or by routinely modifying techniques known in the art.

In certain embodiments, the anti-VEGF antibodies of the invention are generated, e.g., by V-gene replacement. V-gene replacement involves the use of a human monoclonal antibody discover platform, e.g., as described in US 2002-0123057 A1, incorporated herein by reference in its entirety, based on the monoclonal expression of recombinant antibodies in mammalian cells. As described in US 2002-0123057 A1, separate libraries of human heavy and light chain immunoglobulin variable genes have been constructed in a vaccinia virus-based vector by the method of "Trimolecular Recombination." Plasmid vectors incorporating constant regions of human heavy chain secreted gamma 1, human heavy chain membrane hound gamma 1, or human light chain were constructed to accommodate cloning human Ig variable region gene segments VH and Vκ and Vλ) in frame. These vectors are based on the plasmid pH 5/tk, in which a vaccinia early/late promoter and multiple cloning sites were inserted into the viral tk gene. The multiple cloning sites were modified appropriately in order to clone in a modified Ig secretory signal peptide and the constant regions of γ1-secreted or γ1-membrane immunoglobulin heavy chains, and κ immunoglobulin light chains. The resulting vectors retain unique cloning sites for inserting the VH and Vκ variable region genes. Throughout this description Vκ is referred to as VL.

In order to take advantage of the increased diversity generated by random pairing of different heavy and light chains, independent libraries of heavy and light chains were constructed, allowing generation of libraries of sufficient complexity that appropriate VH/VL combinations would occur at a frequency that permits efficient isolation of antibodies with a desired specificity and affinity. The independent assortment of germline V (D) and J segments, as well as the random combinatorial association of VL and VH, provides substantial diversity. Further diversification occurs during the response to antigen by the process of somatic mutation. To take advantage of all diversification processes, libraries produced from four different human B cell sources can be used: 1) commercially obtained bone marrow-derived mRNA from large donor pools, 2) commercially available peripheral blood B cells isolated from cancer patients 3) commercially available peripheral blood B cells, and Bone Marrow from autoimmune patients (ex. Lupus), and 4) tonsil-derived germinal center B cells. Because heavy and light chains are randomly re-assorted in this system, it is possible to generate novel specificities that are more diverse than those of the antigen-driven B cells from which these V genes derive. Somatic hypermutation in the germinal centers and selection resulting from the disease states of the B cell donors contributes greatly to V gene diversity.

Mammalian cells infected with vaccinia immunoglobulin gene recombinant vectors produce fully functional, bivalent antibodies. As outlined above, Ig-H libraries have been generated in a vaccinia expression vector that encodes the secretory form of the human gamma 1 heavy chain constant region. Co-infection of cells with these immunoglobulin heavy chain gene libraries and light chain libraries results in expression, assembly and secretion of bivalent IgG1/L antibodies, permitting screening by ELISA. By infecting host cells with multiplicity of infection (moi)=1 for both Ig-H and Ig-L vaccinia recombinants, each cell is on average infected with one Ig-H and one Ig-L recombinant vaccinia virus and thus expresses a single monoclonal antibody.

Hybridoma technology has been used to identify a number of rodent antibodies with specificity, affinity and functional activity towards important drug targets. For drug development these antibodies are often chimerized or humanized, with the attendant risk of immunogenicity and potential loss of affinity. The V gene replacement strategy has been applied to use of vaccinia virus expressed antibody libraries for conversion of rodent antibodies into fully human or mostly human antibodies.

The concept of V gene replacement in this application is to use a non-human antibody as a template and, through a two-step process, to identify human V genes that can replace the non-human V genes, while still retaining affinity and epitope specificity. The V gene replacement method is thus an alternative to traditional CDR grafted humanization. This method has several advantages compared to the more traditional humanization methods:

(i) V gene replacement results in the selection of fully human antibodies, while retaining the epitope specificity of the non-human MAb. In principle, these antibodies should have a lower risk of immunogenicity compared to CDR grafted and framework modified antibodies that retain significant amounts of murine sequences.

(ii) V gene replacement results in the selection of multiple antibodies. This allows for the selection of lead antibodies derived from distinct VH and VL germline genes with different biochemical properties including CDR sequences, expression levels, pI, etc.

(iii) V gene replacement can result in the selection of antibodies with better affinity and functional activity than the original non-human antibody.

In the first step of the V gene replacement method, the V genes from the non-human antibody are isolated and engineered to create chimeric heavy and light chains. The non-human Ig-His paired with a library of human Ig-L and screened for specific binding to antigen. This initial selection yields a panel of hybrid antibodies comprising chimeric Ig-H and human Ig-L. The selected human Ig-Ls are then paired with a library of human Ig-H and selected for binding to antigen. Parallel selections can also be carried out starting with the non-human Ig-L to select human Ig-H, and then using the selected Ig-H to select human Ig-L. The human Ig-L selected with the chimeric Ig-H, and the human Ig-H selected with the chimeric Ig-L can also be cross-paired. The end result of these selection strategies is that panels of human antibodies that bind to the same antigen as the original non-human antibody are isolated. In most cases, the selected human antibodies recognize the same epitope as the original non-human antibody. If necessary, the first generation human antibodies can be affinity improved through either additional rounds of V gene replacement, or through mutagenesis.

Anti-VEGF antibodies (e.g., MAb 7392) may be selected based on the sustained or improved binding affinity and/or anti-VEGF activity that is imparted to an anti-VEGF antibody compared to a humanized or murine antibody to VEGF. "Anti-VEGF activity" or "VEGF blocking activity" can include activity that modulates one or more of the following activities associated with VEGF: angiogenesis; binding to cell VEGF receptors, including VEGFR1 and VEGFR2; modulating phosphorylation of VEGFR2; or any other activity association with soluble VEGF or VEGF that is bound, e.g., to the extracellular matrix. Anti-VEGF activity can also be attributed to a decrease in incidence or severity of diseases associated with VEGF expression, including, but not limited to, various types of neoplastic disorders, including solid tumors and hematological malignancies, autoimmune diseases, intraocular diseases, and inflammatory diseases. Further optimizing modifications may involve replacement of amino acid residues within one or more CDR and/or framework region such that an anti-VEGF antibody retains specificity for the VEGF antigen and has improved binding affinity and/or improved anti-VEGF activity.

IV. Polynucleotides Encoding Anti-VEGF Antibodies

The present invention also provides for nucleic acid molecules encoding anti-VEGF antibodies of the invention, or antigen-binding fragments, variants, or derivatives thereof.

In one embodiment, the present invention provides an isolated polynucleotide comprising, consisting essentially of, or consisting of a nucleic acid encoding an immunoglobulin heavy chain variable domain (VH domain), where at least one of the CDRs of the VH domain has an amino acid sequence that is at least about 95%, about 96%, about 97%, about 98%, about 99%, or identical to a polynucleotide sequence selected from the group consisting of SEQ ID NO:11, SEQ ID NO:12, or SEQ ID NO:13.

In other embodiments, the present invention provides an isolated polynucleotide comprising, consisting essentially of, or consisting of a nucleic acid encoding an immunoglobulin VH domain, where at least one of the CDRs of the VH domain is selected from the group consisting of: (a) a CDR1 comprising the amino acid sequence set forth in SEQ ID NO:3; (b) a CDR2 comprising the amino acid sequence set forth in SEQ ID NO:4; and (c) a CDR3 comprising the amino acid sequence set forth in SEQ ID NO:5.

In a further embodiment, the present invention includes an isolated polynucleotide comprising, consisting essentially of, or consisting of a nucleic acid encoding a VH domain that has an amino acid sequence that is at least about 95%, about 96%, about 97%, about 98%, about 99%, or 100% identical to a reference VH domain polypeptide sequence comprising SEQ ID NO:1, wherein an anti-VEGF antibody comprising the encoded VH domain specifically or preferentially binds to VEGF, more specifically, human VEGF.

In one embodiment, the present invention provides an isolated polynucleotide comprising, consisting essentially of, or consisting of a nucleic acid encoding an immunoglobulin light chain variable domain (VL domain), where at least one of the CDRs of the VL domain has an amino acid sequence that is at least about 95%, about 96%, about 97%, about 98%, about 99%, or identical to a polynucleotide sequence selected from the group consisting of SEQ ID NO:14, SEQ ID NO:15, and SEQ ID NO:16.

In other embodiments, the present invention provides an isolated polynucleotide comprising, consisting essentially of, or consisting of a nucleic acid encoding an immunoglobulin VL domain, where at least one of the CDRs of the VL domain is selected from the group consisting of: (a) a CDR1 comprising the amino acid sequence set forth in SEQ ID NO:6; (b) a CDR2 comprising the amino acid sequence set forth in SEQ ID NO:7; and (c) a CDR3 comprising the amino acid sequence set forth in SEQ ID NO:8.

In a further embodiment, the present invention includes an isolated polynucleotide comprising, consisting essentially of, or consisting of a nucleic acid encoding a VL domain that has an amino acid sequence that is at least about 95%, about 96%, about 97%, about 98%, about 99%, or 100% identical to a reference VL domain polypeptide sequence comprising SEQ ID NO:2, wherein an anti-VEGF antibody comprising the encoded VL domain specifically or preferentially binds to VEGF.

Any of the polynucleotides described above may further include additional nucleic acids, encoding, e.g., a signal peptide to direct secretion of the encoded polypeptide, antibody constant regions as described herein, or other heterologous polypeptides as described herein. Also, as described in more detail elsewhere herein, the present invention includes compositions comprising one or more of the polynucleotides described above.

In one embodiment, the invention includes compositions comprising a first polynucleotide and second polynucleotide wherein said first polynucleotide encodes a VH domain as described herein and wherein said second polynucleotide encodes a VL domain as described herein. Specifically a composition which comprises, consists essentially of, or consists of a VH domain-encoding polynucleotide, as set forth in SEQ ID NO:1, and a VL domain-encoding polynucleotide, for example, a polynucleotide encoding the VL domain as set forth in SEQ ID NO:2.

Polynucleotides encoding anti-VEGF antibody variable regions include the following:

The H7230 and L7104 variable regions have the following nucleotide sequences (CDRs are underlined):

```
H7230 (SEQ ID NO: 9):
CAGGTGCAGCTGGTGCAGTCTGGGGCTGAATTGAGGAAGCCTGGGGCCTCAGTGAAAATTTCCTGCAAGGC

TTCTGGATACAGCTTGACATACTATGGTATGAATTGGGTGCGACAGGCCCCCGGACAAGGGCTTGAGTGGA

TGGGATGGATCAACACCTTCACTGGGGACTCAACGTATGCCCAGGACTTCACAGGACGGTTTGTCTTCTCC

TTGGACACCTCTGTCAGCACGGCATATCTGCAGATCAGCAGCCTAAAGGCTGAGGACATGGCCATGTATTA

CTGCGCCAAGTACCCTCACTACTACGGCAGCAGCCACTGGTACTTCGACGTGTGGGGCCAGGGCACCACGG

TCACCGTCTCCTCA

L7104 (SEQ ID NO 10):
GAAATTGTGTTGACGCAGTCTCCAGCCACCCTGTCTGTGTCTCCAGGGGAAAGAGCCACCCTCTCCTGCAG

GGCCAGTCAGAGTGTTAACAGCAACTTAGCCTGGTACCAGCAGAAACCTGGCCAGGCTCCCAGGGTCCTCA

TCTATGGTGCTTCCACCAGGGCCACTGGCATCCCAGCCAGGTTCAGTGGCAGTGGGTCTGGGACAGAGTTC

ACTCTCACCATCAGCAGCCTGCAGTCTGAGGATTTTGCAGTTTATTACTGTCAGCAATATAGTGATATCCC

GTGGACGTTCGGCCAGGGGACCAAACTCGAGATCAAA
```

The CDRs of MAb 7392 have the following nucleotide sequences:

```
VH-CDR1 (SEQ ID NO: 11):
GGATACAGCTTGACATACTATGGTATGAAT

VH-CDR2 (SEQ ID NO: 12):
TGGATCAACACCTTCACTGGGGACTCAACGTATGCCCAGGACTTCACAG
GA

VH-CDR3 (SEQ ID NO: 13):
TACCCTCACTACTACGGCAGCAGCCACTGGTACTTCGACGTG

VL-CDR1 (SEQ ID NO: 14):
AGGGCCAGTCAGAGTGTTAACAGCAACTTAGCC

VL-CDR2 (SEQ ID NO: 15):
GGTGCTTCCACCAGGGCCACT

VL-CDR3 (SEQ ID NO: 16):
CAGCAATATAGTGATATCCCGTGGACG
```

The present invention also includes fragments of the polynucleotides of the invention, as described elsewhere. Additionally polynucleotides that encode fusion polypolypeptides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-VEGF antibody, or antigen-binding fragment, variant, or derivative thereof of the invention, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other anti-VEGF antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-VEGF antibody. Amplified nucleic acids generated by PCR may then be cloned into replicable cloning vectors using any method well known in the art.

Once the nucleotide sequence and corresponding amino acid sequence of the anti-VEGF antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) MOLECULAR CLONING, A LABORATORY MANUAL (2nd ed.; Cold Spring Harbor Laboratory, Cold Spring Harbor, N.Y.) and Ausubel et al., eds. (1998) CURRENT PROTOCOLS IN MOLECULAR BIOLOGY (John Wiley & Sons, NY), which are both incorporated by reference herein in their entireties), to generate antibodies having a different amino acid sequence, for example to create amino acid substitutions, deletions, and/or insertions.

A polynucleotide encoding an anti-VEGF binding molecule, e.g., an antibody, or antigen-binding fragment, variant, or derivative thereof, can be composed of any polyribonucleotide or polydeoxyribonucleotide, which may be unmodified RNA or DNA or modified RNA or DNA. For example, a polynucleotide encoding anti-VEGF antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-VEGF binding molecule, e.g., an antibody, or antigen-binding fragment, variant, or derivative thereof can be composed of triple-stranded regions comprising RNA or DNA or both RNA and DNA. A polynucleotide encoding an anti-VEGF binding molecule, e.g., antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. Fusion Proteins and Antibody Conjugates

As discussed in more detail elsewhere herein, anti-VEGF binding molecules, e.g., antibodies of the invention, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-VEGF antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-VEGF antibodies of the invention, or antigen-binding fragments, variants, or derivatives thereof, may include derivatives that are modified, i.e., by the covalent attachment of any type of molecule to the antibody such that covalent attachment does not prevent the antibody binding anti-VEGF. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-VEGF binding molecules, e.g., antibodies of the invention, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. For example, anti-VEGF antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the anti-VEGF binding molecule, including the peptide backbone, the amino acid sidechains and the amino or carboxyl termini, or on moieties such as carbohydrates. It will be appreciated that the same type of modification may be present in the same or varying degrees at several sites in a given anti-VEGF binding molecule. Also, a given anti-VEGF binding molecule may contain many types of modifications. Anti-VEGF binding molecules may be branched, for example, as a result of ubiquitination, and they may be cyclic, with or without branching. Cyclic, branched, and branched cyclic anti-VEGF binding molecules may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Posttranslational Covalent Modification of Proteins (Academic Press, NY), pgs. 1-12; Seifter et al., *Meth. Enzymol.* 182:626-646 (1990); Rattan et al., *Ann. NY Acad. Sci.* 663:48-62 (1992)).

The present invention also provides for fusion proteins comprising an anti-VEGF antibody, or antigen-binding fragment, variant, or derivative thereof, and a heterologous polypeptide. The heterologous polypeptide to which the antibody is fused may be useful for function or is useful to target the anti-VEGF polypeptide expressing cells.

In one embodiment, a fusion protein of the invention comprises, consists essentially of, or consists of, a polypeptide having the amino acid sequence of any one or more of the VH domains of an antibody of the invention or the amino acid sequence of any one or more of the VL domains of an antibody of the invention or fragments or variants thereof, and a heterologous polypeptide sequence.

In another embodiment, a fusion protein for use in the diagnostic and treatment methods disclosed herein comprises, consists essentially of, or consists of a polypeptide having the amino acid sequence of any one, two, three of the CDRs of the VH domain of an anti-VEGF antibody, or fragments, variants, or derivatives thereof, or the amino acid sequence of any one, two, three of the CDRs of the VL domain an anti-VEGF antibody, or fragments, variants, or derivatives thereof, and a heterologous polypeptide sequence. In one embodiment, a fusion protein comprises a polypeptide having the amino acid sequence of at least one VH domain of an anti-VEGF antibody of the invention and the amino acid sequence of at least one VL domain of an anti-VEGF antibody of the invention or fragments, derivatives or variants thereof, and a heterologous polypeptide sequence. Preferably, the VH and VL domains of the fusion protein correspond to a single source antibody (or scFv or Fab fragment) that specifically binds at least one epitope of VEGF. In yet another embodiment, a fusion protein for use in the diagnostic and treatment methods disclosed herein comprises a polypeptide having the amino acid sequence of any one, two, three or more of the CDRs of the VH domain of an anti-VEGF antibody and the amino acid sequence of any one, two, three or more of the CDRs of the VL domain of an anti-VEGF antibody, or fragments or variants thereof, and a heterologous polypeptide sequence. Preferably, two, three, four, five, six, or more of the CDR(s) of the VH domain or VL domain correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349:164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol. Vol.* 115, Abstract No. 1448 (1991)).

As discussed elsewhere herein, anti-VEGF binding molecules, e.g., antibodies of the invention, or antigen-binding fragments, variants, or derivatives thereof, may be fused to heterologous polypeptides to increase the in vivo half life of the polypeptides or for use in immunoassays using methods known in the art. For example, in one embodiment, PEG can be conjugated to the anti-VEGF antibodies of the invention to increase their half-life in vivo. See Leong et al., *Cytokine* 16:106 (2001); Adv. in Drug Deliv. Rev. 54:531 (2002); or Weir et al., *Biochem. Soc. Transactions* 30:512 (2002).

Moreover, anti-VEGF binding molecules, e.g., antibodies of the invention, or antigen-binding fragments, variants, or derivatives thereof, can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116, 964 and 5,225,538). The precise site at which the fusion is made may be selected empirically to optimize the secretion or binding characteristics of the fusion protein. DNA encoding the fusion protein is then transfected into a host cell for expression.

Anti-VEGF binding molecules, e.g., antibodies of the present invention, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-VEGF binding molecules, e.g., antibodies of the invention, or antigen-binding fragments, variants, or derivatives thereof, can be labeled or conjugated either before or after purification, or when purification is performed.

In particular, anti-VEGF antibodies of the invention, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-isothiocyanate. Conjugates of the anti-VEGF antibodies of the invention, or antigen-binding fragments, variants, or derivatives thereof, are prepared in an analogous manner.

The present invention further encompasses anti-VEGF binding molecules, e.g., antibodies of the invention, or antigen-binding fragments, variants, or derivatives thereof, conjugated to a diagnostic or therapeutic agent. The anti-VEGF antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. For example, detection can be facilitated by coupling the anti-VEGF antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{121}$I, $^{131}$I, $^{111}$In, $^{90}$Y, or $^{99}$Tc.

An anti-VEGF binding molecule, e.g., an antibody, or antigen-binding fragment, variant, or derivative thereof, may be conjugated to a therapeutic moiety such as a cytotoxin, a therapeutic agent or a radioactive metal ion. A cytotoxin or cytotoxic agent includes any agent that is detrimental to cells.

An anti-VEGF binding molecule, e.g., an antibody, or antigen-binding fragment, variant, or derivative thereof, also can be detectably labeled by coupling it to a chemiluminescent compound. The presence of the chemiluminescent-tagged anti-VEGF binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-VEGF antibody, or antigen-binding fragment, variant, or derivative thereof, can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md.; Diagnostic Horizons 2:1-7 (1978); Voller et al., *J. Clin. Pathol.* 31:507-520 (1978); Butler, *Meth. Enzymol.* 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-VEGF antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the anti-VEGF binding molecule, e.g., antibody, or antigen-binding fragment, variant, or derivative thereof, it is possible to detect the binding molecule through the use of a radioimmunoassay (MA) (see, for example, Weintraub (March, 1986) Principles of Radioimmunoassays, Seventh Training Course on Radioligand Assay Techniques (The Endocrine Society), which is incorporated by reference herein). The radioactive isotope can be detected by means including, but not limited to, a gamma counter, a scintillation counter, or autoradiography.

An anti-VEGF binding molecule, e.g., antibody, or antigen-binding fragment, variant, or derivative thereof, can also be detectably labeled using fluorescence emitting metals such as 152Eu, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an antibody (e.g., an anti-VEGF antibody), or antigen-binding fragment, variant, or derivative thereof, are well known, see, e.g., Amon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al. (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al. (1982) "The Preparation and Cytotoxic Properties of Antibody-Toxin Conjugates," Immunol. Rev. 62:119-58.

VI. Expression of Antibody Polypeptides

DNA sequences that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide anti-VEGF antibodies, or antigen-binding fragments, variants, or derivatives thereof, of the invention, the polynucleotides encoding the anti-VEGF antibodies are typically inserted in an expression vector for introduction into host cells that may be used to produce the desired quantity of anti-VEGF antibody.

Recombinant expression of an antibody, or fragment, derivative or analog thereof, e.g., a heavy or light chain of an antibody that binds to a target molecule described herein, e.g., VEGF, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthesized as discussed above. Of course, any expression vector that is capable of eliciting expression in eukaryotic cells may be used in the present invention. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-VEGF antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al., *Cell* 11:223 (1977)), hypoxanthine-guanine phosphoribosyltransferase (Szybalska and Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad Sci. USA* 78:1527 (1981)); gpt, which confers resistance to mycophenolic acid (Mulligan and Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); TIB TECH 11 (5):155-215 (May, 1993); and hygro, which confers resistance to hygromycin (Santerre et al., *Gene* 30:147 (1984). Methods commonly known in the art of recombinant DNA technology which can be used are described in Ausubel et al. (1993) Current Protocols in Molecular Biology (John Wiley & Sons, NY); Kriegler (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-VEGF antibodies, or antigen-binding fragments, variants, or derivatives thereof of the invention can also be expressed in non-mammalian cells such as insect, bacteria or yeast or plant cells. Bacteria that readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye and Inouye, *Nucleic Acids Res.* 13:3101-3109 (1985); Van Heeke and Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., *Nature* 282:39 (1979); Kingsman et al., *Gene* 7:141 (1979); Tschemper et al., *Gene* 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. Patent Application Publication No. 2002 0123057 A1.

VII. Treatment Methods Using Therapeutic Anti-VEGF Antibodies

Methods of the invention are directed to the use of anti-VEGF binding molecules, e.g., antibodies, including antigen-binding fragments, variants, and derivatives thereof, to treat patients having a disease associated with VEGF, e.g., soluble VEGF secreted from a cell, or bound VEGF, e.g., attached to an extracellular matrix component. By "VEGF-expressing cell" is intended normal and malignant cells expressing VEGF antigen. Methods for detecting VEGF expression in cells are well known in the art and include, but are not limited to, PCR techniques, immunohistochemistry, flow cytometry, Western blot, ELISA, and the like.

Though the following discussion refers to diagnostic methods and treatment of various diseases and disorders with an anti-VEGF antibody of the invention, the methods described herein are also applicable to the antigen-binding fragments, variants, and derivatives of these anti-VEGF antibodies that retain the desired properties of the anti-VEGF antibodies of the invention, e.g., capable of specifically binding VEGF and having VEGF neutralizing, blocking, and/or inhibiting activity.

In one embodiment, treatment includes the application or administration of an anti-VEGF binding molecule, e.g., an antibody or antigen binding fragment thereof, of the current invention to a patient, or application or administration of the anti-VEGF binding molecule to an isolated tissue or cell line from a patient, where the patient has a disease, a symptom of a disease, or a predisposition toward a disease. In another embodiment, treatment is also intended to include the application or administration of a pharmaceutical composition comprising the anti-VEGF binding molecule, e.g., an antibody or antigen binding fragment thereof, of the current invention to a patient, or application or administration of a pharmaceutical composition comprising the anti-VEGF binding molecule to an isolated tissue or cell line from a patient, who has a disease, a symptom of a disease, or a predisposition toward a disease.

The anti-VEGF binding molecules, e.g., antibodies or binding fragments thereof, of the present invention are useful for the treatment of various malignant and non-malignant tumors. By "anti-tumor activity" is intended a reduction in the rate of malignant VEGF-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. For example, therapy with at least one anti-VEGF antibody causes a physiological response, for example, a reduction in angiogenesis, that is beneficial with respect to treatment of disease states associated with VEGF expression in a human.

In one embodiment, the invention relates to anti-VEGF binding molecules, e.g., antibodies or binding fragments thereof, according to the present invention for use as a medicament, in particular for use in the treatment or prophylaxis of cancer or for use in a precancerous condition or lesion. In certain embodiments, an anti-VEGF binding molecule, e.g., an antibody or binding fragment thereof, of the invention is used for the treatment of a VEGF over-expressing cancer or a cancer in which VEGF expression leads to increased angiogenesis and/or tumor growth. In certain embodiments, an anti-VEGF binding molecule, e.g., an antibody or binding fragment thereof, of the invention is used for the treatment of a solid tumor, such as colorectal cancer, renal cell carcinoma, glioblastoma, lung cancer (including non-small cell lung carcinoma), and breast cancer.

Further, anti-VEGF binding molecules, e.g., antibodies or binding fragments thereof, of the present invention can also be used to inhibit angiogenesis for the treatment of pathological conditions dependent upon the formation of new blood vessels, including tumor development and macular degeneration. Angiogenesis is a complex multistep morphogenetic event during which endothelial cells, stimulated by major determinants of vascular remodeling, dynamically modify their cell-to-cell and cell-to-matrix contacts and move directionally to be reorganized into a mature vascular tree (Bussolino et al., *Trends Biochem Sci.* 22:251-256 (1997); Risau, *Nature* 386:671-674 (1997); Jain, *Nat. Med.* 9:685-693 (2003)). The formation of new blood vessels is a key step during embryo development, but it also occurs in adults in physiologic and in pathologic conditions, such as retinopathy, rheumatoid arthritis, ischemia, and particularly tumor growth and metastasis (Carmeliet, *Nat. Med.* 9:6:3-660 (2003)). This pathological formation of new blood vessels is also herein referred to as "invasive angiogenesis."

In accordance with the methods of the present invention, at least one anti-VEGF binding molecule, e.g., an antibody or antigen binding fragment thereof, as defined elsewhere herein is used to promote a positive therapeutic response with respect to a malignant human cell. By "positive therapeutic response" with respect to cancer treatment is intended an improvement in the disease in association with the anti-tumor activity of these binding molecules, e.g., antibodies or fragments thereof, and/or an improvement in the symptoms associated with the disease. That is, a decrease in tumor vasculature, a reduction in tumor size, an anti-proliferative effect, the prevention of further tumor outgrowths, a reduction in the number of cancer cells, and/or a decrease in one or more symptoms associated with the disease can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only. Other positive therapeutic responses include an increase in the period of progression-free patient survival, an increase in the period of time to progression, and an increase in the period of overall patient survival.

Tumor response can be assessed for changes in tumor morphology (i.e., overall tumor burden, tumor cell count, and the like) using screening techniques such as bioluminescent imaging, for example, luciferase imaging, bone scan imaging, and tumor biopsy sampling including bone marrow aspiration (BMA). In addition to these positive therapeutic responses, the subject undergoing therapy with the anti-VEGF binding molecule, e.g., an antibody or antigen-binding fragment thereof, may experience the beneficial effect of an improvement in the symptoms associated with the disease. For example, the subject may experience a decrease in the so-called B symptoms, e.g., night sweats, fever, weight loss, and/or urticaria.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-VEGF binding molecule, e.g., an antibody or antigen-binding fragment thereof, may experience the beneficial effect of an improvement in the symptoms associated with the disease.

The anti-VEGF binding molecules, e.g., antibodies or antigen binding fragments thereof, can be used in combination with at least one other cancer therapy, including, but not limited to, surgery or surgical procedures (e.g. splenectomy, hepatectomy, lymphadenectomy, leukophoresis, bone marrow transplantation, and the like); radiation therapy; chemotherapy, or other cancer therapy; where the additional cancer therapy is administered prior to, during, or subsequent to the anti-VEGF binding molecule, e.g., antibody or antigen binding fragment thereof, therapy. Thus, where the combined therapies comprise administration of an anti-VEGF binding molecule, e.g., an antibody or antigen binding fragment thereof, of the invention in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass coadministration, using separate formulations or a single pharmaceutical formulation, or and consecutive administration in either order. Examples of chemotherapy that may be used in combination with the anti-VEGF binding molecules, e.g., antibodies or antigen binding fragments thereof, include, but are not limited to taxane, paclitaxel, carboplatin, 5-fluorouracil, leucovorin, capecitabine, oxaliplatin, irinotecan, or any combination thereof.

A further embodiment of the invention is the use of anti-VEGF binding molecule, e.g., antibodies or antigen binding fragments thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

The anti-VEGF antibodies for use in the treatment methods described above in this section are intended to include those anti-VEGF antibodies, or, fragments, variants, or derivatives that are described in detail elsewhere herein as if they were separately listed in this section.

VIII. Pharmaceutical Compositions and Administration Methods

Methods of preparing and administering the anti-VEGF binding molecule, e.g., antibodies, or antigen-binding fragments, variants, or derivatives thereof, of the invention to a subject in need thereof are well known to or are readily determined by those skilled in the art. The route of administration of the anti-VEGF binding molecule, e.g., antibody, or antigen-binding fragment, variant, or derivative thereof, may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, anti-VEGF binding molecules, e.g., antibodies, or antigen-binding fragments, variants, or derivatives thereof, of the invention can be delivered directly to the site of the adverse cellular population thereby increasing the exposure of the diseased tissue to the therapeutic agent.

As discussed herein, anti-VEGF binding molecules, e.g., antibodies, or antigen-binding fragments, variants, or derivatives thereof, of the invention may be administered in a pharmaceutically effective amount for the in vivo treatment of VEGF-expression-mediated diseases such as neoplastic disorders, including solid tumors. In this regard, it will be appreciated that the disclosed binding molecules of the invention will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-VEGF binding molecule, e.g., an antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-VEGF antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. patent application Ser. No. 09/259,337. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an anti-VEGF binding molecule, e.g., antibody, or fragment, variant, or derivative thereof, that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, anti-VEGF antibodies, or antigen-binding fragments, variants, or derivatives thereof of the invention may be administered to a human or other animal in accordance with the aforementioned methods of treatment in an amount sufficient to produce a therapeutic effect. The anti-VEGF antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-VEGF binding molecules, e.g., antibodies, or antigen-binding fragments, variants, or derivatives thereof, of the invention may prove to be particularly effective.

By "therapeutically effective dose or amount" or "effective amount" is intended an amount of anti-VEGF binding molecule, e.g., antibody or antigen binding fragment thereof, that when administered brings about a positive therapeutic response with respect to treatment of a patient with a disease to be treated.

Therapeutically effective doses of the compositions of the present invention, for treatment of VEGF-expression-mediated diseases such as neoplastic disorders, including solid tumors, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one anti-VEGF binding molecule, e.g., antibody or binding fragment thereof, to be administered is readily determined by one of ordinary skill in the art without undue experimentation given the disclosure of the present invention. Factors influencing the mode of administration and the respective amount of at least one anti-VEGF binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-VEGF binding molecule, e.g., antibody, or fragment, variant, or derivative thereof, to be administered will be dependent upon the mode of administration and whether the subject will undergo a single dose or multiple doses of this agent.

The present invention also provides for the use of an anti-VEGF binding molecule, e.g., an antibody or antigen-binding fragment, variant, or derivative thereof, in the manufacture of a medicament for treating a neoplastic disorder (e.g., a solid tumor or a hematological malignancy) or an autoimmune or inflammatory disease or an intraocular neovasculature syndrome.

The invention also provides for the use of an anti-VEGF binding molecule, e.g., antibody of the invention, or antigen-binding fragment, variant, or derivative thereof, in the manufacture of a medicament for treating a subject with a neoplastic disorder (including solid tumors), wherein the medicament is used in a subject that has been pretreated with at least one other therapy. By "pretreated" or "pretreatment" is intended the subject has received one or more other therapies (e.g., been treated with at least one other cancer therapy) prior to receiving the medicament comprising the anti-VEGF binding molecule, e.g., antibody or antigen-binding fragment, variant, or derivative thereof. "Pretreated" or "pretreatment" includes subjects that have been treated with at least one other therapy within a period of time prior to initiation of treatment with the medicament comprising the anti-VEGF binding molecule, for example, the monoclonal antibody MAb 7392 disclosed herein, or antigen-binding fragment, variant, or derivative thereof. It is not necessary that the subject was a responder to pretreatment with the prior therapy or therapies. Thus, the subject that receives the medicament comprising the anti-VEGF binding molecule, e.g., an antibody or antigen-binding fragment, variant, or derivative thereof could have responded, or could have failed to respond (e.g., the cancer was refractory), to pretreatment with the prior therapy, or to one or more of the prior therapies where pretreatment comprised multiple therapies. Examples of other cancer therapies for which a subject can have received pretreatment prior to receiving the medicament comprising the anti-VEGF binding molecule, e.g., antibody or antigen-binding fragment, variant, or derivative thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy; small molecule-based cancer therapy, including, but not limited to, the small molecules listed herein above; vaccine/immunotherapy-based cancer therapies; steroid therapy; other cancer therapy; or any combination thereof.

The anti-VEGF antibodies for use in the pharmaceutical compositions and administration methods described above in this section are intended to include those anti-VEGF antibodies, or fragments, variants, or derivatives that are described in detail elsewhere herein as if they were separately listed in this section.

IX. Diagnostics

The invention further provides a diagnostic method useful during diagnosis of VEGF-mediated diseases such as neoplastic disorders, including solid tumors, which involves measuring the expression level of VEGF protein or transcript in tissue or other cells or body fluid from an individual and comparing the measured expression level with a standard VEGF expression level in normal tissue or body fluid, whereby an increase in the expression level compared to the standard is indicative of a disorder.

The anti-VEGF antibodies of the invention and antigen-binding fragments, variants, and derivatives thereof, can be used to assay VEGF protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting VEGF protein expression include immunoassays, such as the enzyme linked immunosorbent assay (ELISA), immunoprecipitation, or Western blotting. Suitable assays are described in more detail elsewhere herein.

By "assaying the expression level of VEGF polypeptide" is intended qualitatively or quantitatively measuring or estimating the level of VEGF polypeptide in a first biological sample either directly (e.g., by determining or estimating absolute protein level) or relatively (e.g., by comparing to the disease associated polypeptide level in a second biological sample). Preferably, VEGF polypeptide expression level in the first biological sample is measured or estimated and compared to a standard VEGF polypeptide level, the standard being taken from a second biological sample obtained from an individual not having the disorder or being determined by averaging levels from a population of individuals not having the disorder. As will be appreciated in the art, once the "standard" VEGF polypeptide level is known, it can be used repeatedly as a standard for comparison.

By "biological sample" is intended any biological sample obtained from an individual, cell line, tissue culture, or other source of cells potentially expressing VEGF. Methods for obtaining tissue biopsies and body fluids from mammals are well known in the art.

The anti-VEGF antibodies for use in the diagnostic methods described above in this section are intended to include those anti-VEGF antibodies, or fragments, variants, or derivatives that are described in detail elsewhere herein as if they were separately listed in this section.

X. Immunoassays

Anti-VEGF antibodies, or antigen-binding fragments, variants, or derivatives thereof of the invention may be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) CURRENT PROTOCOLS IN MOLECULAR BIOLOGY (John Wiley & Sons, Inc., NY) Vol. 1, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, (1994) Current Protocols in Molecular Biology (John Wiley & Sons, Inc., NY) Vol. 1 at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$, or $^{125}I$ diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, (1994) Current Protocols in Molecular Biology (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) Current Protocols in Molecular Biology (John Wiley & Sons, Inc., NY) Vol. 1 at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

Anti-VEGF antibodies, or antigen-binding fragments, variants, or derivatives thereof of the invention, additionally, can be employed histologically, as in immunofluorescence, immunoelectron microscopy or non-immunological assays, for in situ detection of VEGF protein or conserved variants or peptide fragments thereof. In situ detection may be accomplished by removing a histological specimen from a patient, and applying thereto a labeled anti-VEGF antibody, or antigen-binding fragment, variant, or derivative thereof, preferably applied by overlaying the labeled antibody (or fragment) onto a biological sample. Through the use of such a procedure, it is possible to determine not only the presence of VEGF protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for VEGF gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to VEGF or conserved variants or peptide fragments thereof, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-VEGF antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-VEGF antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pairwise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The anti-VEGF antibodies for use in the immunoassays described above in this section are intended to include those anti-VEGF antibodies, or fragments, variants, or derivatives that are described in detail elsewhere herein as if they were separately listed in this section.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the Treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd, ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J. Immunology: The Science of Self-Nonself Discrimination (John Wiley & Sons, NY); Kennett et al., eds. (1980). Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988). Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1

Selection and Characterization of MAb 7392 Anti-VEGF Antibody

The VH and VK genes from mouse anti-VEGF antibody A.4.6.1 were engineered into an Ig-H and Ig-K in vaccinia virus so that they could be expressed as a chimeric antibody with a human IgG1 heavy chain constant region and a human kappa light chain constant region.

The chimeric, VEGF-specific immunoglobulin light chain (Ig-L) was screened in combination with the human immunoglobulin heavy chain (Ig-H) mini-libraries. Thus, in a single well there were nominally 100-1000 distinct VH/VL combinations. Each assay well contained about 100,000 cells that were infected at a multiplicity of infection (moi)=1 for Ig-H and Ig-K.

Following incubation for 72-96 hr, culture supernatants were sampled and tested by ELISA for capacity to bind to VEGF that had been coated onto an ELISA plate. Mini Ig-H libraries corresponding to positive wells were sampled from the master plate and re-plated at limiting dilution (e.g., 10 pfu/well).

Following second round screening, individual plaques from each positive well were picked and amplified. This step generates monoclonal vaccinia virus immunoglobulin heavy chain (vvIg-H) constructs.

HeLa cell monolayers were then coinfected with each monoclonal Ig-H and Ig-K pair. The resulting supernatants were tested for antigen binding to verify that correct pairs of VH and VL that encode for specific Ab were obtained. The VH genes were PCR amplified and subcloned into mammalian expression vectors for high level expression and further analysis.

To select human VL that can pair with the human VHs the process was reversed. The selected human Ig-Hs were used to screen mini-libraries of human Ig-K gene libraries, each containing a pool of 100-1000 individual VK gene recombinants in association with CH as described above.

The antibody selection strategy can be broken down into the following steps as described in FIG. 1.

Step 1: The VH and VK genes from a murine anti-VEGF antibody A.4.6.1 were engineered into vaccinia virus so that they would be expressed as chimeric human IgG1/kappa.

Step 2: A Human Ig-H Library was created where the CDR3 from the mouse MAb was grafted onto a library of human VH genes. Every clone in the resulting Ig-H library contains the CDR3 from the anti-VEGF MAb, with diversity in the rest of the VH gene.

Step 3: The chimeric anti-VEGF Ig-K was used to select human Ig-Hs from the CDR3-grafted library that can pair with the chimeric Ig-K and retain VEGF specific binding.

Step 4: The V genes from the selected vaccinia Ig-H recombinants were cloned and select mutations were made in the CDRs for affinity improvement.

Step 5: This affinity improved heavy chain was engineered back into vaccinia virus and used to select human Ig-Ks that can pair and retain VEGF specific binding.

Step 6: The V genes from the selected vaccinia recombinants were cloned into mammalian expression vectors containing the gamma I and kappa constant domains, creating full length gamma I heavy and kappa light chain genes. Recombinant antibody was produced by co-transfecting the plasmids containing the full length heavy and light chain genes into CHO cells.

Step 7: Recombinant antibody was purified by Protein A chromatography.

Step 8: Additional mutations were made on heavy and light chain CDRs, as well as framework regions Step 9: Antibodies were tested for specificity, affinity, and functionality.

MAb7392 was selected as the best anti-VEGF antibody. MAb7392 is the combination of H7230 and L7104, which have the following amino acid sequences (CDRs are underlined):

H7230 (SEQ ID NO: 1):
QVQLVQSGAELRKPGASVKISCKASGYSLTYYGMNWVRQAPGQGLEWMG

WINTFTGDSTYAQDFTGRFVFSLDTSVSTAYLQISSLKAEDMAMYYCAK

YPHYYGSSHWYFDVWGQGTTVTVSS

L7104 (SEQ ID NO: 2):
EIVLTQSPATLSVSPGERATLSCRASQSVNSNLAWYQQKPGQAPRVLIY

GASTRATGIPARFSGSGSGTEFTLTISSLQSEDFAVYYCQQYSDIPWTF

GQGTKLEIK

The CDRs of MAb 7392 have the following amino acid sequences:

```
VH-CDR1 (SEQ ID NO: 3):
GYSLTYYGMN

VH-CDR2 (SEQ ID NO: 4):
WINTFTGDSTYAQDFTG

VH-CDR3 (SEQ ID NO: 5):
YPHYYGSSHWYFDV

VL-CDR1 (SEQ ID NO: 6):
RASQSVNSNLA

VL-CDR2 (SEQ ID NO: 7):
GASTRAT

VL-CDR3 (SEQ ID NO: 8):
QQYSDIPWT
```

The H7230 and L7104 variable regions have the following nucleotide sequences (CDRs are underlined):

H7230 (SEQ ID NO: 9):

CAGGTGCAGCTGGTGCAGTCTGGGGCTGAATTGAGGAAGCCTGGGGCCTCAGTGAAAATTTCCTGCAAGGC

TTCTGGATACAGCTTGACATACTATGGTATGAATTGGGTGCGACAGGCCCCCGGACAAGGGCTTGAGTGGA

TGGGATGGATCAACACCTTCACTGGGGACTCAACGTATGCCCAGGACTTCACAGGACGGTTTGTCTTCTCC

TTGGACACCTCTGTCAGCACGGCATATCTGCAGATCAGCAGCCTAAAGGCTGAGGACATGGCCATGTATTA

CTGCGCCAAGTACCCTCACTACTACGGCAGCAGCCACTGGTACTTCGACGTGTGGGGCCAGGGCACCACGG

TCACCGTCTCCTCA

L7104 (SEQ ID NO: 10):

GAAATTGTGTTGACGCAGTCTCCAGCCACCCTGTCTGTGTCTCCAGGGGAAAGAGCCACCCTCTCCTGCAG

GGCCAGTCAGAGTGTTAACAGCAACTTAGCCTGGTACCAGCAGAAACCTGGCCAGGCTCCCAGGGTCCTCA

TCTATGGTGCTTCCACCAGGGCCACTGGCATCCCAGCCAGGTTCAGTGGCAGTGGGTCTGGGACAGAGTTC

ACTCTCACCATCAGCAGCCTGCAGTCTGAGGATTTTGCAGTTTATTACTGTCAGCAATATAGTGATATCCC

GTGGACGTTCGGCCAGGGGACCAAACTCGAGATCAAA

The CDRs of MAb 7392 have the following nucleotide sequences:

```
VH-CDR1 (SEQ ID NO: 11):
GGATACAGCTTGACATACTATGGTATGAAT

VH-CDR2 (SEQ ID NO: 12):
TGGATCAACACCTTCACTGGGGACTCAACGTATGCCCAGGACTTCACAG
GA

VH-CDR3 (SEQ ID NO: 13):
TACCCTCACTACTACGGCAGCAGCCACTGGTACTTCGACGTG

VL-CDR1 (SEQ ID NO: 14):
AGGGCCAGTCAGAGTGTTAACAGCAACTTAGCC

VL-CDR2 (SEQ ID NO: 15):
GGTGCTTCCACCAGGGCCACT

VL-CDR3 (SEQ ID NO: 16):
CAGCAATATAGTGATATCCCGTGGACG
```

Example 2

Biacore Data

MAb7392 was tested by Biacore for affinity. VEGF was immobilized on the chip. Bevacizumab (commercially known as Avastin®) and MAb7392 were passed over VEGF or control surface at varying concentrations. Data was fit with a bivalent model for affinity determination. As shown in Table 2, the affinity measured by Biacore is superior to that of bevacizumab.

TABLE 2

Biacore affinity values for VEGF antibodies.

|  | Affinity (nM) |
|---|---|
| MAb7392 | 0.91 |
| Bevacizumab | 3.9 |

Example 3

Epitope Competition Assay

MAb7392 and bevacizumab share an epitope on VEGF. This was determined by the ability of MAb7392 to prevent the binding of bevacizumab to VEGF. Briefly, titrated MAb7392 and biotinylated bevacizumab were added to a VEGF-coated plate. Any biotinylated bevacizumab able to bind was detected with Strep-HRP. Blocking ability was proportional to affinity to VEGF. As shown in FIG. 2, MAb 7392 was able to block the binding of biotinylated bevacizumab to VEGF better than bevacizumab could. This demonstrates the conservation of epitope specificity and increased affinity of MAb 7392.

Example 4

VEGFR1 Blocking ELISA

MAb7392 can prevent VEGF from binding to VEGFR1. Titrated VEGF-specific antibodies were pre-incubated with VEGF and then added to a VEGFR1-coated ELISA plate. Any VEGF that was free to bind to the ELISA plate was detected with an independent biotinylated anti-VEGF polyclonal antibody. As shown in FIG. 3 and Table 3, the ability of MAb7392 to block VEGF from binding to VEGFR1 is superior to that of bevacizumab.

TABLE 3

VEGFR1 blocking assay IC50

|  | nM [MAb] for 50% Blocking |
|---|---|
| MAb7392 | 0.08 |
| Bevacizumab | 0.40 |

Example 5

VEGFR2 Blocking ELISA

MAb7392 can prevent VEGF from binding to VEGFR2. Titrated VEGF specific antibodies were pre-incubated with VEGF and then added to a VEGFR2 coated plate. Any VEGF that is free to bind to the ELISA plate is detected with an independent biotinylated anti-VEGF polyclonal antibody. As shown in FIG. 4 and Table 4, the ability of MAb7392 to block VEGF from binding to VEGFR2 was superior to that of bevacizumab.

TABLE 4

VEGFR2 blocking assay

|  | nM [MAb] for 50% Blocking |
|---|---|
| MAb7392 | 0.18 |
| Bevacizumab | 0.26 |

Example 6

VEGFR2 Phosphorylation Assay

VEGF binding to VEGFR2 leads to autophosphorylation of VEGFR2. The addition of a VEGF specific antibody disrupts this phosphorylation. MAb7392 can prevent the phosphorylation of VEGFR2 in a titratable manner.

A line of 293 cells stably over-expressing VEGFR2 was made using standard transfection methods. This cell line was then used for the VEGFR2 phosphorylation assay.

100 ng/mL of VEGF was preincubated with titrated amounts of VEGF-specific antibodies. This was then added to 293 cells stably overexpressing VEGFR2 for 10 minutes. Cells were then lysed and amount of VEGFR2 phosphorylation was determined by ELISA. As shown in FIG. 5, MAb 7392 is comparable to bevacizumab in the ability to block VEGFR2 phosphorylation.

Example 7

IHC Staining of Normal Human Arrays

On a human tissue array, containing 34 different tissue types, mAb7392 IHC testing demonstrates comparable tissue cross-reactivity as bevacizumab.

Example 8

Treatment of Established A673 Xenografts

A673 is a human rhabdomyosarcoma cell line. The growth of this cell line in xenograft model has been documented by literature. Five million cells in matrigel were injected i.p. into the dorsal area of 4-6 week old female CD-1 nude mice. On day 7 following grafting, tumors were measured and mice regrouped based on tumor size, 12 mice per group. Starting size of tumors on day 7 ranged from 100-200 mm³. Drug treatment was 100 ug, 2 times per week for a total of 5 doses. The dosing schedule is shown in Table 5.

TABLE 5

Dosing of CD1 Nude Mice Xenograft Models

| Group | Drug | Dosing Schedule |
|---|---|---|
| 1 | 100 μg hIgG | 2X/week for 5 100-150 mm³ |
| 2 | 100 μg bevacizumab | 2X/week for 5 doses from 100-150 mm³ |
| 3 | 100 μg mAb7392 | 2X/week for 5 doses from 100-150 mm³ |

The study was terminated three weeks after the final dose. As shown in FIG. 6, MAb 7392 is comparable to bevacizumab in the ability to delay growth of A673 xenografts.

SUMMARY

The present inventors have generated a novel VEGF antibody with confirmed functionality in both in vitro and in vivo assays. In a superior manner than bevacizumab, MAb7392 prevents VEGF from binding to its receptors, VEGFR1 and VEGFR2. With an affinity of 0.91 nM, MAb7392 is approximately 4-fold better than bevacizumab, when tested under the same conditions. MAb7392 prevents the VEGF-induced phosphorylation of VEGFR2. MAb7392 delays the growth of A673 xenografts in vivo. This antibody has also been confirmed for specificity by ELISA and flow-based assays, as well as by IHC.

TABLE 6

Summary of MAb7392 Characterization Mab 7392

| Affinity | Affinity is 0.9 nM<br>Affinity of MAb7392 is several fold better than bevacizumab |
|---|---|
| in vitro function | a. VEGFR1 blocking assay<br>b. VEGFR2 blocking assay<br>c. VEGFR2 phosphorylation assay<br>MAb7392 is similar or better than bevacizumab in all assays tested |
| in vivo function | Inhibition of A673 xenograft growth<br>MAb7392 exhibits similar tumor inhibition as bevacizumab |
| specificity | MAb7392 has confirmed specificity to VEGF |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An isolated antibody or antigen-binding fragment thereof that specifically binds to human VEGF, wherein the variable heavy chain domain (VH) of said antibody or antigen-binding fragment thereof comprises a Kabat heavy chain complementarity determining region-3 (VH-CDR3) amino acid sequence identical to SEQ ID NO:5, a Chothia-Kabat heavy chain complementarity determining region-1 (VH-CDR1) amino acid sequence identical to SEQ ID NO:3, a Kabat heavy chain complementarity determining region-2 (VH-CDR2) amino acid sequence identical to SEQ ID NO:4; and a variable light chain domain (VL) of said antibody or antigen-binding fragment thereof comprises a Kabat light chain complementarity determining region-1 (VL-CDR1) amino acid sequence identical to SEQ ID NO:6, a Kabat light chain complementarity determining region-2 (VL-CDR2) amino acid sequence identical to SEQ ID NO:7, and a Kabat light chain complementarity determining region-3 (VL-CDR3) amino acid sequence identical to SEQ ID NO:8.

2. The antibody or antigen-binding fragment thereof according to claim 1, wherein said antibody is MAb 7392 or an antigen-binding fragment thereof or wherein said antibody or fragment thereof competitively inhibits reference monoclonal antibody MAb 7392 from specifically binding to VEGF.

3. The antibody or antigen-binding fragment thereof according to claim 1, wherein the VH of said antibody or fragment thereof comprises the amino acid sequence of SEQ ID NO:1.

4. The antibody or antigen-binding fragment thereof according to claim 1, wherein the VL of said antibody or fragment thereof comprises the amino acid sequence of SEQ ID NO:2.

5. The antibody or antigen-binding fragment thereof according to claim 1, wherein the VH and VL of said antibody or fragment thereof comprise amino acid sequences identical to SEQ ID NO:1 and SEQ ID NO:2, respectively.

6. The antibody or antigen-binding fragment thereof according to claim 1, which is an Fab fragment, an F(ab)$_2$ fragment, an Fv fragment, or a single chain antibody.

7. The antibody or antigen-binding fragment thereof according to claim 1, which comprises a light chain constant region selected from the group consisting of a human kappa constant region and a human lambda constant region.

8. The antibody or antigen-binding fragment thereof according to claim 1, which comprises a heavy chain constant region or a fragment thereof.

9. The antibody or antigen-binding fragment thereof according to claim 8, wherein said heavy chain constant region or fragment thereof is human IgG1, IgG2, IgG3, IgG4, IgM, IgA1, IgA2, IgE or IgD.

10. The antibody or antigen-binding fragment thereof according to claim 1, which inhibits VEGF from binding to a VEGF receptor.

11. The antibody or antigen-binding fragment thereof according to claim 10, wherein said VEGF receptor is selected from the group consisting of VEGFR1 and VEGFR2.

12. The antibody or antigen-binding fragment thereof according to claim 1, which inhibits phosphorylation of VEGFR2 by VEGF.

13. The antibody or antigen-binding fragment thereof according to claim 1, further comprising a heterologous polypeptide fused thereto.

14. The antibody or antigen-binding fragment thereof according to claim 1, wherein said antibody or fragment thereof is further conjugated to at least one agent selected from the group consisting of a cytotoxic agent, a therapeutic agent, a cytostatic agent, a biological toxin, a prodrug, an enzyme, a lipid, a biological response modifier, a lymphokine, a heterologous antibody or fragment thereof, a detectable label, and polyethylene glycol (PEG).

15. The antibody or antigen-binding fragment thereof according to claim 14, wherein said at least one cytotoxic agent is selected from the group consisting of a radionuclide, a biotoxin, and an enzymatically active toxin.

16. The antibody or antigen-binding fragment thereof according to claim 14, wherein said at least one detectable label is selected from the group consisting of an enzyme, a fluorescent label, a chemiluminescent label, a bioluminescent label, and a radioactive label.

17. A composition comprising the antibody or antigen-binding fragment thereof according to claim 1, and a carrier.

18. The composition of claim 17, wherein said carrier is selected from the group consisting of saline, buffered saline, dextrose, water, and glycerol.

19. A method for neutralizing VEGF in an animal, said method comprising administering to said animal a composition comprising:
  (a) the isolated antibody or antigen-binding fragment thereof of claim 1; and
  (b) a pharmaceutically acceptable carrier.

20. A method for treating a cancer in an animal in need of treatment, said method comprising administering to said animal a composition comprising:
  (a) the isolated antibody or antigen-binding fragment thereof of claim 1; and
  (b) a pharmaceutically acceptable carrier.

21. A method for inhibiting angiogenesis in an animal in need of treatment for cancer, said method comprising administering to said animal a composition comprising:
  (a) the isolated antibody or antigen-binding fragment thereof of claim 1; and
  (b) a pharmaceutically acceptable carrier.

22. The method of claim 20, wherein said cancer is a solid tumor.

23. The method of claim 20, wherein said cancer is selected from the group consisting of colorectal cancer, lung cancer, renal cell carcinoma, breast cancer, non-small cell lung cancer, and glioblastoma.

24. The method of claim 20, wherein said cancer is metastatic.

25. The method of claim 20, wherein said cancer is non-resectable.

26. The method according to claim 20, wherein said method further comprises administering to said animal at least one additional therapy.

27. The method of claim 26, wherein said at least one additional therapy is selected from the group consisting of radiation therapy and chemotherapy.

28. The method of claim 27, wherein said at least one additional therapy is a chemotherapy selected from the group consisting of taxane, paclitaxel, carboplatin, 5-flurouracil, leucovorin, capecitabine, oxaliplatin, and irinotecan.

29. The method of claim 20, wherein said antibody or antigen-binding fragment thereof inhibits VEGF binding to a VEGF receptor.

30. The method of claim 29, wherein said VEGF receptor is VEGFR1 or VEGFR2.

31. The method of claim 20, wherein said antibody or antigen-binding fragment thereof inhibits phosphorylation of VEGFR2 by VEGF.

32. The method of claim 20, wherein said animal is a human.

33. The antibody or antigen-binding fragment according to claim 1, wherein the light chain constant region is a human kappa constant region.

34. The antibody or antigen-binding fragment according to claim 9, wherein the heavy chain constant region or fragment thereof is human IgG1.

* * * * *

SEQUENCE LISTING

```
<160> NUMBER OF SEQ ID NOS: 16

<210> SEQ ID NO 1
<211> LENGTH: 123
<212> TYPE: PRT
<213> ORGANISM: Artificial Sequence
<220> FEATURE:
<223> OTHER INFORMATION: H7230 Heavy chain variable region

<400> SEQUENCE: 1

Gln Val Gln Leu Val Gln Ser Gly Ala Glu Leu Arg Lys Pro Gly Ala
1               5                   10                  15

Ser Val Lys Ile Ser Cys Lys Ala Ser Gly Tyr Ser Leu Thr Tyr Tyr
            20                  25                  30

Gly Met Asn Trp Val Arg Gln Ala Pro Gly Gln Gly Leu Glu Trp Met
        35                  40                  45

Gly Trp Ile Asn Thr Phe Thr Gly Asp Ser Thr Tyr Ala Gln Asp Phe
    50                  55                  60
```

```
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Met Ala Met Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Thr Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: L7104 Light Chain variable region

<400> SEQUENCE: 2

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Asn Ser Asn
             20                  25                  30

Leu Ala Trp Tyr Gln Gln Lys Pro Gly Gln Ala Pro Arg Val Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Asp Ile Pro Trp
                 85                  90                  95

Thr Phe Gly Gln Gly Thr Lys Leu Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: H7230 VH-CDR1

<400> SEQUENCE: 3

Gly Tyr Ser Leu Thr Tyr Tyr Gly Met Asn
 1               5                  10

<210> SEQ ID NO 4
<211> LENGTH: 17
<212> TYPE: PRT
<213> ORGANISM: Artificial Sequence
<220> FEATURE:
<223> OTHER INFORMATION: H7230 VH-CDR2

<400> SEQUENCE: 4

Trp Ile Asn Thr Phe Thr Gly Asp Ser Thr Tyr Ala Gln Asp Phe Thr
 1               5                  10                  15

Gly

<210> SEQ ID NO 5
<211> LENGTH: 14
<212> TYPE: PRT
<213> ORGANISM: Mus musculus

<400> SEQUENCE: 5
```

Tyr Pro His Tyr Tyr Gly Ser Ser His Trp Tyr Phe Asp Val
1               5                   10

<210> SEQ ID NO 6
<211> LENGTH: 11
<212> TYPE: PRT
<213> ORGANISM: Artificial Sequence
<220> FEATURE:
<223> OTHER INFORMATION: L7104 VL-CDR1

<400> SEQUENCE: 6

Arg Ala Ser Gln Ser Val Asn Ser Asn Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: L7104 VL-CDR2

<400> SEQUENCE: 7

Gly Ala Ser Thr Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: L7104 VL-CDR3

<400> SEQUENCE: 8

Gln Gln Tyr Ser Asp Ile Pro Trp Thr
1               5

<210> SEQ ID NO 9
<211> LENGTH: 369
<212> TYPE: DNA
<213> ORGANISM: Artificial Sequence
<220> FEATURE:
<223> OTHER INFORMATION: H7230 Heavy chain variable region

<400> SEQUENCE: 9
caggtgcagc tggtgcagtc tggggctgaa ttgaggaagc ctggggcctc agtgaaaatt      60
tcctgcaagg cttctggata cagcttgaca tactatggta tgaattgggt gcgacaggcc     120
cccggacaag ggcttgagtg gatgggatgg atcaacacct tcactgggga ctcaacgtat     180
gcccaggact tcacaggacg gtttgtcttc tccttggaca cctctgtcag cacggcatat     240
ctgcagatca gcagcctaaa ggctgaggac atggccatgt attactgcgc caagtaccct     300
cactactacg gcagcagcca ctggtacttc gacgtgtggg gccagggcac cacggtcacc     360
gtctcctca                                                             369

<210> SEQ ID NO 10
<211> LENGTH: 321
<212> TYPE: DNA
<213> ORGANISM: Artificial Sequence
<220> FEATURE:
<223> OTHER INFORMATION: L7104 Light chain variable region

<400> SEQUENCE: 10
gaaattgtgt tgacgcagtc tccagccacc ctgtctgtgt ctccagggga aagagccacc      60

```
ctctcctgca gggccagtca gagtgttaac agcaacttag cctggtacca gcagaaacct    120
ggccaggctc ccagggtcct catctatggt gcttccacca gggccactgg catcccagcc    180
aggttcagtg gcagtgggtc tgggacagag ttcactctca ccatcagcag cctgcagtct    240
gaggattttg cagtttatta ctgtcagcaa tatagtgata tcccgtggac gttcggccag    300
gggaccaaac tcgagatcaa a                                              321

<210> SEQ ID NO 11
<211> LENGTH: 30
<212> TYPE: DNA
<213> ORGANISM: Artificial Sequence
<220> FEATURE:
<223> OTHER INFORMATION: H7230 VH-CDR1

<400> SEQUENCE: 11
ggatacagct tgacatacta tggtatgaat                                      30

<210> SEQ ID NO 12
<211> LENGTH: 51
<212> TYPE: DNA
<213> ORGANISM: Artificial Sequence
<220> FEATURE:
<223> OTHER INFORMATION: H7230 VH-CDR2

<400> SEQUENCE: 12
tggatcaaca ccttcactgg ggactcaacg tatgcccagg acttcacagg a               51

<210> SEQ ID NO 13
<211> LENGTH: 42
<212> TYPE: DNA
<213> ORGANISM: Artificial Sequence
<220> FEATURE:
<223> OTHER INFORMATION: H7230 VH-CDR3

<400> SEQUENCE: 13
taccctcact actacggcag cagccactgg tacttcgacg tg                        42

<210> SEQ ID NO 14
<211> LENGTH: 33
<212> TYPE: DNA
<213> ORGANISM: Artificial Sequence
<220> FEATURE:
<223> OTHER INFORMATION: L7104 VL-CDR1

<400> SEQUENCE: 14
agggccagtc agagtgttaa cagcaactta gcc                                  33

<210> SEQ ID NO 15
<211> LENGTH: 21
<212> TYPE: DNA
<213> ORGANISM: Artificial Sequence
<220> FEATURE:
<223> OTHER INFORMATION: L7104 VL-CDR2

<400> SEQUENCE: 15
ggtgcttcca ccagggccac t                                               21

<210> SEQ ID NO 16
<211> LENGTH: 27
<212> TYPE: DNA
<213> ORGANISM: Artificial Sequence
```

```
<220> FEATURE:
<223> OTHER INFORMATION: L7104 VL-CDR3

<400> SEQUENCE: 16
cagcaatata gtgatatccc gtggacg                                              27
```